(12) United States Patent
Gleba et al.

(10) Patent No.: US 7,652,194 B2
(45) Date of Patent: Jan. 26, 2010

(54) PROCESSES AND VECTORS FOR PRODUCING TRANSGENIC PLANTS

(75) Inventors: Yuri Gleba, Halle (DE); Victor Klimyuk, Halle (DE); Gregor Benning, Halle (DE); Serik Eliby, Halle (DE)

(73) Assignee: Icon Genetics GmbH, Munich (DE)

( * ) Notice: Subject to any disclaimer, the term of this patent is extended or adjusted under 35 U.S.C. 154(b) by 195 days.

(21) Appl. No.: 10/416,931

(22) PCT Filed: Dec. 7, 2001

(86) PCT No.: PCT/EP01/14421

§ 371 (c)(1),
(2), (4) Date: Dec. 24, 2003

(87) PCT Pub. No.: WO02/46440

PCT Pub. Date: Jun. 13, 2002

(65) Prior Publication Data

US 2004/0088764 A1    May 6, 2004

(30) Foreign Application Priority Data

Dec. 8, 2000 (DE) .................. 100 61 150

(51) Int. Cl.
*C12N 15/82* (2006.01)
*C12N 15/40* (2006.01)

(52) U.S. Cl. ............ 800/278; 800/288; 536/23.72; 536/24.1

(58) Field of Classification Search ............ 435/91.41, 435/320.1, 69.1, 468; 536/24.1; 800/278
See application file for complete search history.

(56) References Cited

U.S. PATENT DOCUMENTS

| | | | |
|---|---|---|---|
| 5,139,812 A | 8/1992 | Lebacq | |
| 5,474,925 A | 12/1995 | Maliyakal et al. | |
| 5,576,198 A | 11/1996 | McBride et al. | |
| 5,627,059 A | 5/1997 | Capecchi et al. | |
| 5,670,623 A | 9/1997 | Shoseyov et al. | |
| 5,723,765 A | 3/1998 | Oliver et al. | |
| 5,877,402 A | 3/1999 | Maliga et al. | |
| 5,922,601 A * | 7/1999 | Baetscher et al. | 435/456 |
| 6,100,448 A | 8/2000 | Thompson et al. | 800/278 |
| 6,147,278 A | 11/2000 | Rogers et al. | |
| 6,147,280 A * | 11/2000 | Smeekens et al. | 800/284 |
| 6,174,700 B1 | 1/2001 | Haynes et al. | |
| 6,300,545 B1 | 10/2001 | Baszczynski et al. | |
| 6,331,416 B1 | 12/2001 | Shani et al. | |
| 6,331,661 B1 | 12/2001 | Baszczynski et al. | |
| 6,781,033 B2 | 8/2004 | Staub et al. | |
| 2003/0188337 A1 | 10/2003 | Day et al. | |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |
| 2005/0014150 A1 | 1/2005 | Atabekov et al. | |
| 2005/0015829 A1 | 1/2005 | Koop et al. | |
| 2005/0015830 A1 | 1/2005 | Dorokhov et al. | |
| 2005/0059004 A1 | 3/2005 | Atabekov et al. | |
| 2005/0066384 A1 | 3/2005 | Klimyuck et al. | |
| 2005/0091706 A1 | 4/2005 | Klimyuck et al. | |

FOREIGN PATENT DOCUMENTS

| | | |
|---|---|---|
| EP | 0270 248 | 6/1988 |
| EP | 1 045 037 | 10/2000 |
| WO | 87/00551 | 1/1987 |
| WO | 94/16089 | 7/1994 |
| WO | 95/34668 | 12/1995 |
| WO | 96/17954 | 6/1996 |
| WO | 98/09505 | 3/1998 |
| WO | WO98/44097 | 10/1998 |
| WO | WO 98/54342 | * 12/1998 |
| WO | WO98/54342 | 12/1998 |
| WO | 99/25821 | 5/1999 |
| WO | 99/25855 | 5/1999 |
| WO | 99/36516 | 7/1999 |
| WO | 01/11020 | 2/2000 |
| WO | 00/17365 | 3/2000 |
| WO | 00/20611 | 4/2000 |
| WO | 00/32799 | 6/2000 |
| WO | 00/68391 | 11/2000 |
| WO | 00/68431 | 11/2000 |
| WO | 00/70019 | 11/2000 |
| WO | 00/77174 | 12/2000 |
| WO | 00/77175 | 12/2000 |
| WO | WO00/78985 | 12/2000 |
| WO | 01/59138 | 8/2001 |
| WO | 01/81600 | 11/2001 |
| WO | WO02/12522 | 2/2002 |
| WO | 02/29068 | 4/2002 |
| WO | WO02/29068 | 4/2002 |
| WO | 02/46438 | 6/2002 |
| WO | 02/46440 | 6/2002 |

(Continued)

OTHER PUBLICATIONS

Parry (1994) Gene 150:105-109).*

(Continued)

*Primary Examiner*—David T Fox
(74) *Attorney, Agent, or Firm*—Myers Bigel Sibley & Sajovec, P.A.

(57) ABSTRACT

This invention describes a process for gene expression in plants utilizing translational vectors. Said translational vectors cause a gene of interest to be stably integrated into a transcriptionally active host genomic DNA such that the transcription of the gene of interest is controlled by a promoter of the host plant. Said translational vectors are preferably based on internal ribosome entry site (IRES) elements that are of plant origin.

2 Claims, 16 Drawing Sheets

FOREIGN PATENT DOCUMENTS

| WO | 02/055651 | 7/2002 |
|---|---|---|
| WO | 02/057466 | 7/2002 |
| WO | 02/068664 | 9/2002 |
| WO | 02/077246 | 10/2002 |
| WO | 02/079481 | 10/2002 |
| WO | 02/088369 | 11/2002 |
| WO | 02/101060 | 12/2002 |
| WO | 03/001900 | 1/2003 |
| WO | 03/004658 | 1/2003 |
| WO | 03/020927 | 3/2003 |
| WO | 03/020928 | 3/2003 |
| WO | 03/020938 | 3/2003 |

OTHER PUBLICATIONS

Parry et al.*

Skulachev et al. (1999) Virology, 263:139-153.*

Toth et al. FEBS Letters, 489:215-219, 2001.*

Topping et al (Insertional Mutagenesis And Promoter Trapping In Plants For The Isolation Of Genes And The Study Of Development. 1995. Transgenic Research 4:291-305.*

Skulachev, et al. Internal initiation of Translation directed by the 5'-Untranslated region of the tobamavirus subgenomic RNA I2.*

Attal et al (The efficiency of different IRESs (Internal Ribosom Entry Site) in monocistronic mRNAs. Molecular Biology Reports (2000) 27:21-26.*

Teeri et al. The EMBO Journal 5(8): 1755-1760 (1986).*

Donson et al. Proc. Natl. Acad. Sci. USA 88: 7204-7208 (Aug. 1991).*

Murakami et al. Gene 202: 23-29 (1997).*

Albert et al. (1995) "Site-specific integration of DNA into wild-type and mutant lox sites placed in the plant genome" The Plant Journal 7:649-659.

Allison et al., "Deletion of rpoB Reveals a Second Distinct Transcription System in Plastids of Higher Plants," The EMBO Journal, 15:11 2802-2809 (1996).

Altschul et al. "Basic Local Alignment Search Tool," J. Mol. Biol., 215:403-410 (1990).

Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.

Bateman et al. (2000) "Tools for chloroplast transformation in Chlamydomonas: expression vectors and a new dominant selectable marker" Mol. Gen. Genet. 263:401-410.

Bergamini et al. "Picornavirus IRESes and the Poly(A) tail Jointly Promote Cap-Independent Translation in a Mammalian Cell-free System," RNA, 6:1781-1790 (2000).

Bogorad, Lawrence, "Engineering Chloroplasts: an Alternative Site for Foreign Genes, Proteins, Reactions and Products," TIBTECH, 18:257-263 (Jun. 2000).

Bouchez et al. (1993) "A binary vector based on Basta resistance for in planta transformation of *Arabidopsis thaliana*" C. R. Acad. Sci. Paris, Science de la vie 316:1188-1193.

Boynton et al., "Chloroplast Transformation in Chlamydomonas with High Velocity Microprojectiles," Science, 240:1534-1538 (1988).

Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present In Linked Multiple Copies Greatly Enhances IRES Activity," PNAS, 97(4):1536-1541 (Feb. 15, 2000).

Clelland et al. (1999) "Hiding Messages in DNA Microdots," Nature 399:533-534.

Coutts et al. "Development of Geminivirus-based Gene Vectors for Dicotyledonous Plants" Australian Journal of Plant Physiology 17:365-375 (1990).

Dale et al. "Intra- and intermolecular site-specific recombination in plant cells mediated by bacteriophage P1 recombinase" Gene 91:79-85 (1990).

Dale et al. "Mutations in the CRE/LOX Recombination Site Enhance the Stability of Recombination Products: Applications for Gene Targeting in Plants" Journal of Cellular Biochemistry 50 (S16S):206 (1992).

Daniell, "New Tools for Chloroplast Genetic Engineering," Nature Biotechnology, 17:855-856 (Sep. 1999).

De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).

Domingo et al. (1999) "Identification of a novel peptide motif that mediates cross-linking of proteins to cell walls" The Plant Journal 20:563-570.

Dorokhov et al. "Polypurine (A)-Rich Sequences Promote Cross-Kingdom Conservation of Internal Ribosome Entry" PNAS 99(8):5301-5306 (Apr. 16, 2002).

Drescher et al., "The Two Largest Chloroplast Genome-Encoded Open Reading Frames of Higher Plants are Essential Genes," The Plant Journal, 22(2):97-104 (2000).

El-Sheekh, M.M. (2000) "Stable Chloroplast Transformation in *Chlamydomonas reinhardtii* using Microprojectile Bombardment" Folia Microbiol. 45(6) 496-504.

Fischer et al., "Selectable Marker Recycling in the Chloroplast," Mol. Gen. Genet., 251:373-380 (1996).

Gatz et al. (1991) "Regulation of a modified CaMV 35S promoter by the Tn10-encoded Tet repressor in transgenic tobacco" Mol. Gen. Genet. 227:229-237.

Hager at al., "Enslaved Bacteria as New Hope for Plant Biotechnologists," Appl. Microbiol. Biotechnol., 54:302-310 (2000).

Heifetz, Peter B., "Genetic Engineering of the Chloroplast," Biochimie, 82:655-666 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IRESs): Reality and Use" Transgenic Research, 8:157-177 (1999).

Iamtham et al. (2000) "Removal of antibiotic resistance genes from transgenic tobacco plastids" 18:1172-1176.

Ivanov et al. "A Tobamovirus Genome That Contains an Internal Ribosome Entry Site Functional In Vitro," Virology, 232:32-43 (1997).

Jeon et al. (2000) "T-DNA insertional mutagenesis for functional genomics in rice" Plant J. 22:561-570.

Kofer et al., "PEG-Mediated Plastid Transformation in Higher Plants," In Vitro Cell. Dev. Biol.-Plant, 31:303-309 (1998).

Koshinsky et al. (2000) "Cre-lox site-specific recombination between *Arabidopsis* and tobacco chromosomes" The Plant Journal 23:715-722.

Kozak, "Initiation of Translation in Prokaryotes and Eukaryotes" Gene 234:187-208 (1999).

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant *staphylococci* on cotton fibers by functional display of a fungal cellulose-binding domain" FEMS Microbiology Letters 195:197-204.

Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use In Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure in Poly(A)-tail-promoted Translation In Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat×Tripsacum Crosses" Crop Science 33:973-976.

Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of *Saccharomyces cerevisiae*" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170 (1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in *Chlamydomonas* chloroplasts" Plant J. 11:635-648.

Suzuki et al., "Engineering of the rp123 Gene Cluster to Replace the Plastid RNA Polymerase Subunit with the *Escherichia coli* Homologue," Curr. Genet., 38:218-225 (2000).

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Urwin et al. (2000) "Functional characterization of the EMCV IRES in plants" Plant J. 24:583-589.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in *Arabidopsis thaliana* by transient expression of cre" Plant Molecular Biology 38:393-406 (1998).

Walden et al. "Gene-transfer and plant regeneration techniques" Trends in Biotechnology 13:324-331 (1995).

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

International Search Report for International Application Serial No. PCT/EP01/11629, mailed Jun. 3, 2002.

International Search Report for International Application Serial No. PCT/EP02/02091, mailed Jun. 19, 2002.

International Search Report corresponding to PCT/EP01/15034; Date of Mailing: Jun. 19, 2002.

International Search Report for International Application Serial No. PCT/EP 02/07134 dated Jun. 27, 2002.

International Search Report corresponding to PCT/EP02/06464; Date of Mailing: Sep. 30, 2002.

International Search Report for International Application Serial No. PCT/EP02/03476, mailed Oct. 21, 2002.

International Search Report corresponding to PCT/EP02/03266; Date of Mailing: Feb. 18, 2003.

International Search Report corresponding to PCT/EP02/09843, mailed May 21, 2003.

International Search Report mailed on Jun. 8, 2003 for application No. PCT/EP EP 02/09605.

International Search Report mailed on Jul. 14, 2003 for application No. PCT/EP EP 02/04777.

International Search Report for application No. PCT/EP02/09844, mailed Jul. 15, 2003.

Derbyshire et al. "Lightning strikes twice: Intron-intein coincidence" Proc. Natl. Acad. Sci. USA 95:1356-1357 (1998).

Lustig et al. "Long Poly(A) Tracts in the Human Genome are Associate with the *Alu* Family of Repeated Elements" J. Mol. Biol. 180:753-759 (1984).

Wu et al. "Markerless Deletions of *pil* Genes in *Myxococcus xanthus* generated by Counterselection with the *Bacillus subtilis sacB* Gene" Journal of Bacteriology 178(19):5817-5281 (1996).

Attal et al.; "The efficiency of different IRESs (Internal Ribosomes Entry Site) in monocistronic mRNAS," Molecular Biology Reports 27: 21-26 (2000).

Topping et al.; "Functional tagging of regulatory elements in the plant genome," Development 12: 1009-1019 (1991).

Topping et al.; "Insertional mutagenesis and promoter trapping in plants for the isolation of genes and the study of development," Transgenic Research 4: 291-305 (1995).

Topping et al.; "Promoter Trap Markers Differentiate Structural and Positional Components of Polar Development in *Arabidopsis*," The Plant Cell 9: 1713-1725 (1997).

Hagemann et al. "Extranuclear Inheritance: Plastid Genetics" Progress in Botany, vol. 55, 260-275 (1994).

Klaus et al. "Generation of Marker Free Plastid Transformants Using a Transiently Cointegrated Selection Gene" Nature Biotechnology 22: 225-229 (2004).

Mühlbauer et al. "Functional analysis of plastid DNA replication origins in tobacco by targeted inactivation" The Plant Journal, 32:175-184 (2002).

Ruf et al. "Stable Genetic Transformation of Tomato Plastids and Expression of a Foreign Protein in Fruit" Nature Biotechnology 19: 870-875 (2001).

Sanz et al. "Altered local and systemic spread of movement deficient virus in transgenic tobacco plants expressing the cucumber mosaic virus 3a protein" Arch Virol. 145:2387-2401 (2000).

Shimada et al. "Fine Structural Features of the Chloroplast Genome: Comparison of the Sequenced Chloroplast Genomes" Nucleic Acids Research 19: 983-995 (1991).

Shinozaki et al. "The Complete Nucleotide Sequence of the Tobacco Chloroplast Genome: Its Gene Organization and Expression" The EMBO Journal 5: 2043-2049 (1986).

Sidorov et al. "Stable Chloroplast Transformation in Potato: Use of Green Fluorescent Protein as a Plastid Marker" The Plant Journal 19: 209-216 (1999).

Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.

Michael et al. (1999) "Efficient gene-specific expression of Cre recombinase in the mous embryo by targeted insertion of a novel IRES-Cre cassette into endogenous loci" Mech. Dev. 85:35-47.

Mountford and Smith (1995) "Internal ribosome entry sites and dicistronic RNAs in mammalian transgenesis" Trends Genet. 11:179-184.

Wells et al. (1999) "Codon optimization, genetic insulation, and rtTA reporter improve performance of the tetracycline switch" Transgenic Res. 8:371-381.

International Search Report for International Application Serial No. PCT/EP01/14421, mailed Nov. 29, 2002.

* cited by examiner pIC 1301 pIC 1451 pIC06-IRES

PROCESSES AND VECTORS FOR PRODUCING TRANSGENIC PLANTS

CROSS-REFERENCE TO RELATED APPLICATIONS

The present application is a 35 U.S.C. §371 National Phase Application of International Application Ser. No. PCT/EP01/14421, filed Dec. 7, 2001 and published in English as PCT Publication No. WO 02/46440 on Jun. 13, 2002, which claims priority to German Patent Application Ser. No. 100 61 150.8, filed Dec. 8, 2000, which status is pending, the disclosures of each of which are incorporated herein by reference in their entireties.

FIELD OF THE INVENTION

The present invention relates to processes and vectors for producing transgenic plants as well as plant cells and plants obtained thereby.

BACKGROUND OF THE INVENTION

Achievement of a desirable and stably inheritable pattern of transgene expression remains one of the major problems in plant biotechnology. The standard approach is to introduce a transgene as part of a fully independent transcription unit using a vector, where the transgene is under transcriptional control of a plant-specific heterologous or a homologous promoter and transcription termination sequences (for example, see U.S. Pat. No. 05,591,605; U.S. Pat. No. 05,977,441; WO 0053762 A2; U.S. Pat. No. 05,352,605, etc). However, after the integration into the genomic DNA, because of random insertion of exogenous DNA into plant genomic DNA, gene expression from such transcriptional vectors becomes affected by many different host factors. These factors make transgene expression unstable, unpredictable and often lead to the transgene silencing in progeny (Matzke & Matzke, 2000, *Plant Mol Biol.*, 43, 401-415; S. B. Gelvin, 1998, *Curr. Opin. Biotechnol.*, 9, 227-232; Vaucheret et al., 1998, *Plant J.*, 16, 651-659). There are well-documented instances of transgene silencing in plants, which include the processes of transcriptional (TGS) and posttranscriptional gene silencing (PTGS). Recent findings reveal a close relationship between methylation and chromatin structure in TGS and involvement of RNA-dependent RNA-polymerase and a nuclease in PTGS (Meyer, P., 2000, *Plant Mol. Biol*, 43, 221-234; Ding, S. W., 2000, *Curr. Opin. Biotechnol.*, 11, 152-156; Iyer et al., *Plant Mol. Biol.*, 2000, 43, 323-346). For example, in TGS, the promoter of the transgene can often undergo methylation at many integration sites with chromatin structure not favorable for stable transgene expression. As a result, practicing existing methods requires many independent transgenic plants to be produced and analyzed for several generations in order to find those with the desired stable expression pattern. Moreover, even such plants displaying a stable transgene expression pattern through the generations can become subsequently silenced under naturally occurring conditions, such as a stress or pathogen attack. Existing approaches aiming at improved expression control, such as use of scaffold attachment regions (Allen, G. C., 1996, *Plant Cell*, 8, 899-913; Clapham, D., 1995, *J. Exp. Bot.*, 46, 655-662; Allen, G. C., 1993, *Plant Cell*, 5, 603-613) flanking the transcription unit, could potentially increase the independency and stability of transgene expression by decreasing dependency from so-called "position effect variation" (Matzke & Matzke, 1998, *Curr. Opin. Plant Biol.*, 1, 142-148; S. B. Gelvin, 1998, *Curr. Opin. Biotechnol.*, 9, 227-232; WO 9844 139 A1; WO 006757 A1; EP 1 005 560 A1; AU 00,018, 331 A1). However, they only provide a partial solution to the existing problem of designing plants with a required expression pattern of a transgene.

Gene silencing can be triggered as a plant defence mechanism by viruses infecting the plant (Ratcliff et al., 1997, *Science*, 276, 1558-1560; Al-Kaff et al., 1998, *Science*, 279, 2113-2115). In non-transgenic plants, such silencing is directed against the pathogen, but in transgenic plants it can also silence the transgene, especially when the transgene shares homology with a pathogen. This is a problem, especially when many different elements of viral origin are used in designing transcriptional vectors. An illustrative example is the recent publication by Al-Kaff and colleagues (Al-Kaff et al., 2000, *Nature Biotech.*, 18, 995-999) who demonstrated that CaMV (cauliflower mosaic virus) infection of a transgenic plant with the BAR gene under the control of the CaMV-derived 35S promoter can silence the transgene.

During the last years, the set of cis-regulatory elements has significantly increased and presently includes tools for sophisticated spatial and temporal control of transgene expression. These include several transcriptional elements such as various promoters and transcription terminators as well as translational regulatory elements/enhancers of gene expression. In general, translation enhancers can be defined as cis-acting elements which, together with cellular trans-acting factors, promote the translation of the mRNA. Translation in eukaryotic cells is generally initiated by ribosome scanning from the 5' end of the capped mRNA. However, initiation of translation may also occur by a mechanism which is independent of the cap structure. In this case, the ribosomes are directed to the translation start codon by internal ribosome entry site (IRES) elements. These elements, initially discovered in picornaviruses (Jackson & Kaminski, 1995, RNA, 1, 985-1000), have also been identified in other viral and cellular eucaryotic mRNAs. IRES are cis-acting elements that, together with other cellular trans-acting factors, promote assembly of the ribosomal complex at the internal start codon of the mRNA. This feature of IRES elements has been exploited in vectors that allow for expression of two or more proteins from polycistronic transcription units in animal or insect cells. At present, they are widely used in bicistronic expression vectors for animal systems, in which the first gene is translated in a cap-dependent manner and the second one is under the control of an IRES element (Mountford & Smith, 1995, *Trends Genet*, 4, 179-184; Martines-Salas, 1999, *Curr Opin Biotech.*, 19, 458-464). Usually the expression of a gene under the control of an IRES varies significantly and is within a range of 6-100% compared to cap-dependent expression of the first one (Mizuguchi et al., 2000, *Mol. Ther.*, 1, 376-382). These findings have important implications for the use of IRESs, for example for determining which gene shall be used as the first one in a bicistronic vector. The presence of an IRES in an expression vector confers selective translation not only under normal conditions, but also under conditions when cap-dependent translation is inhibited. This usually happens under stress conditions (viral infection, heat shock, growth arrest, etc.), normally because of the absence of necessary trans-acting factors (Johannes & Sarnow, 1998, *RNA*, 4, 1500-1513; Sonenberg & Gingras, 1998, *Cur. Opin. Cell Biol.*, 10, 268-275).

Translation-based vectors recently attracted attention of researchers working with animal cell systems. There is one report connected with the use of an IRES-Cre recombinase cassette for obtaining tissue-specific expression of cre recombinase in mice (Michael et al., 1999, *Mech. Dev.*, 85, 35-47).

In this work, a novel IRES-Cre cassette was introduced into the exon sequence of the EphA2 gene, encoding an Eph receptor of protein tyrosine kinase expressed early in development. This work is of specific interest as it is the first demonstration of the use of translational vectors for tissue-specific expression of a transgene in animal cells that relies on transcriptional control of the host DNA. Another important application for IRES elements is their use in vectors for the insertional mutagenesis. In such vectors, the reporter or selectable marker gene is under the control of an IRES, element and can only be expressed if it inserts within the transcribed region of a transcriptionally active gene (Zambrowich et al., 1998, *Nature*, 392, 608-611; Araki et al., 1999, *Cell Mol. Biol.*, 45, 737-750). However, despite the progress made in the application of IRESs in animal systems, IRES elements from these systems are not functional in plant cells. Moreover, since site-directed or homologous recombination in plant cells is extremely rare and of no practical use, similar approaches with plant cells were not contemplated.

There are significantly less data about plant-specific IRES elements. Recently, however, several IRESs that are also active in plants were discovered in tobamovirus crTMV (a TMV virus infecting Cruciferae plants) (Ivanov et al., 1997, *Virology*, 232, 32-43; Skulachev et al., 1999, *Virology*, 263, 139-154; WO 98/54342) and there are indications of IRES translation control in other plant viruses (Hefferon et al., 1997, *J. Gen Virol.*, 78, 3051-3059; Niepel & Gallie, 1999, *J. Virol*, 73, 9080-9088). IRES technology has a great potential for the use in transgenic plants and plant viral vectors providing convenient alternative to existing vectors. Up to date, the only known application of plant IRES elements for stable nuclear transformation is connected with the use of IRESs to express a gene of interest in bicistronic constructs (WO 98/54342). The construct in question comprises, in 5' to 3' direction, a transcription promoter, the first gene linked to the said transcription promoter, an IRES element located 3' to the first gene and the second gene located 3' to the IRES element, i.e., it still contains a full set of transcription control elements.

Surprisingly, we have found that translational vectors that are devoid of their own transcription control elements and rely entirely on insertion into a transcriptionally active genomic DNA of a plant host, allow recovery of numerous transformants which express the gene of interest. Even more surprisingly, such transformants could be easily detected even in host plants with a very low proportion of transcriptionally active DNA in their genome such as wheat. This invention is the basis of the proposed process that allows for design of transgene expression that is entirely controlled by the host's transcriptional machinery, thus minimizing the amount of xenogenetic regulatory DNA elements known to trigger transgene silencing. It also allows to control transgene expression in a novel way, by modulating the ratio of cap-dependent versus cap-independent translation.

A—the vector contains a translation enhancer and a translation stop codon;

B—the vector contains an IRES as translation enhancer and a transcription termination region;

C—as in B, except that the IRES is preceded by translation stop codons for all three reading frames;

D—as in C, except that the vector is flanked by intron/exon boundary regions (3'I-5'E and 3'E-5'I) to provide the features of an exon and to facilitate its incorporation into the spliced mRNA.

Figure 1A:
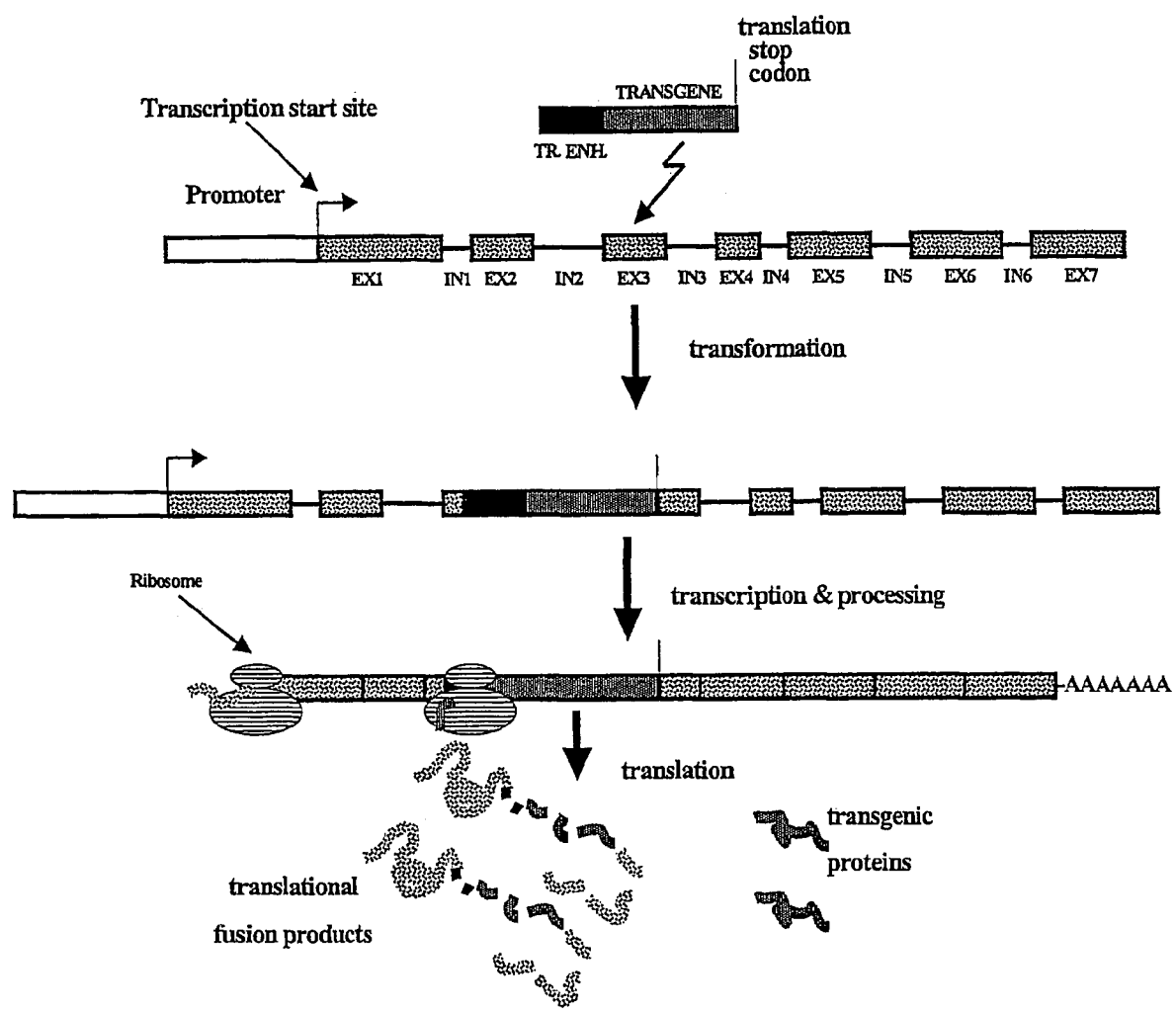
FIG. 1 shows transgene expression from four of many possible translational vector variants.
Figure 1B:
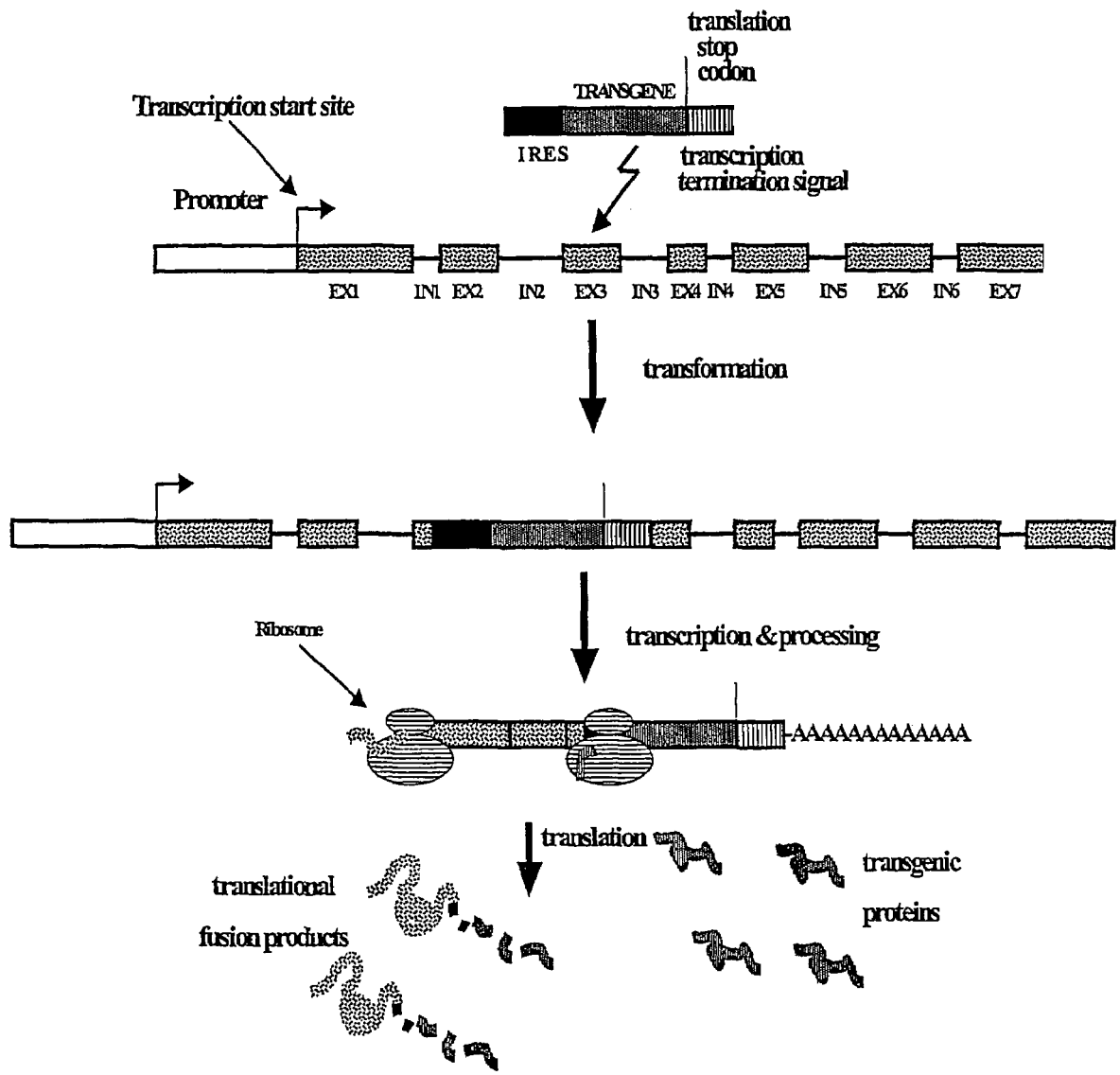
Figure 1C:
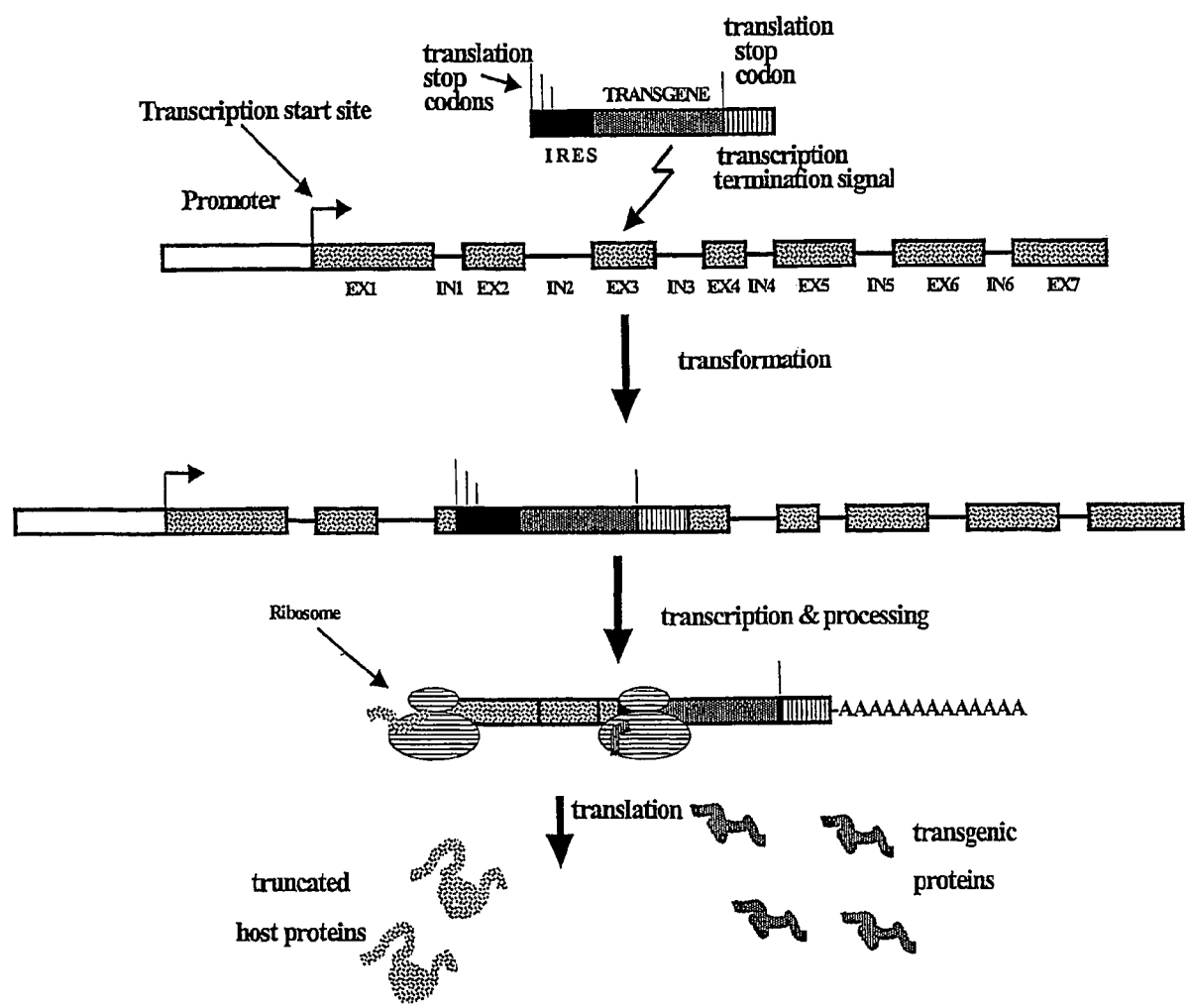
Figure 1D:
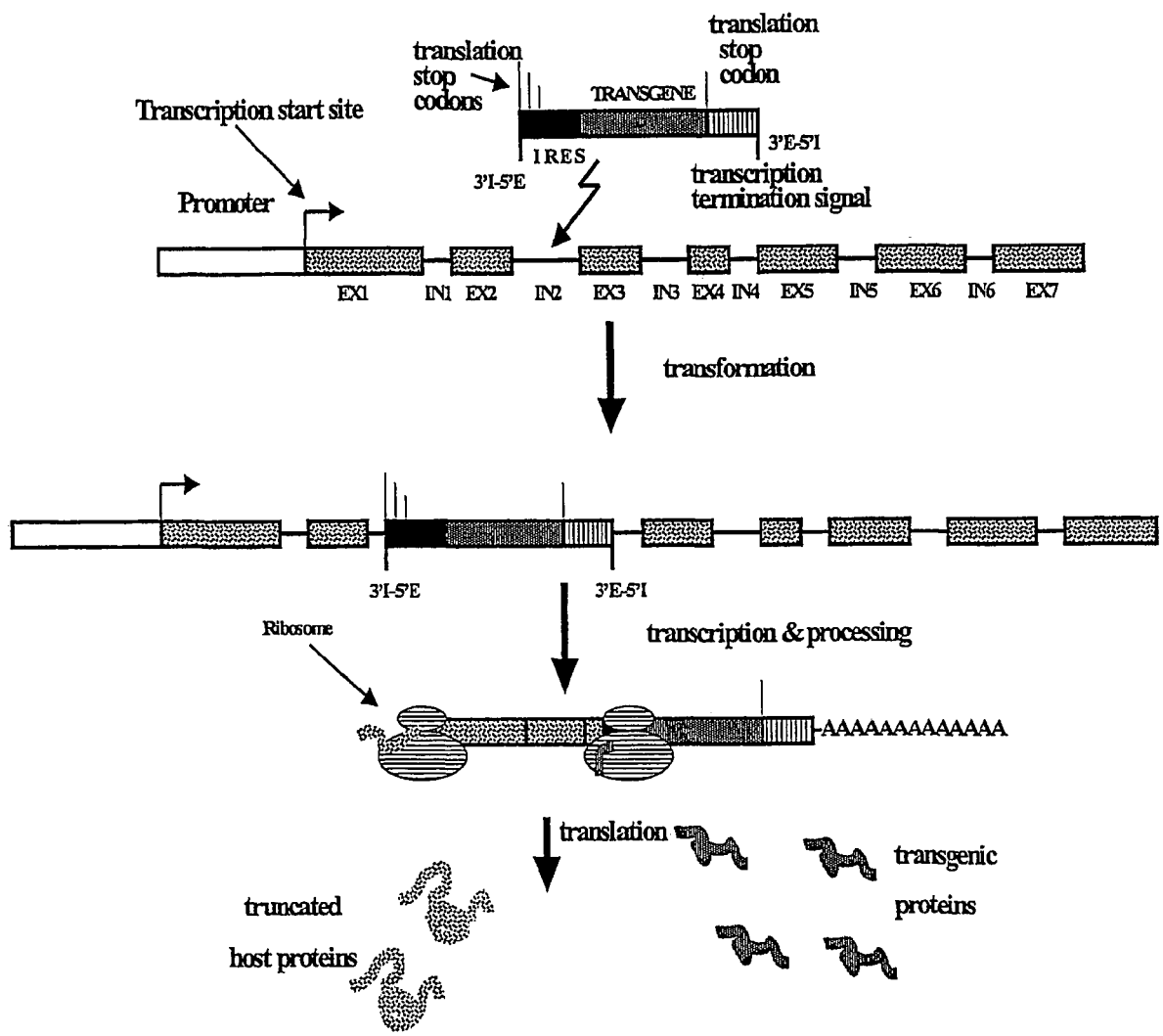
Figure 2:
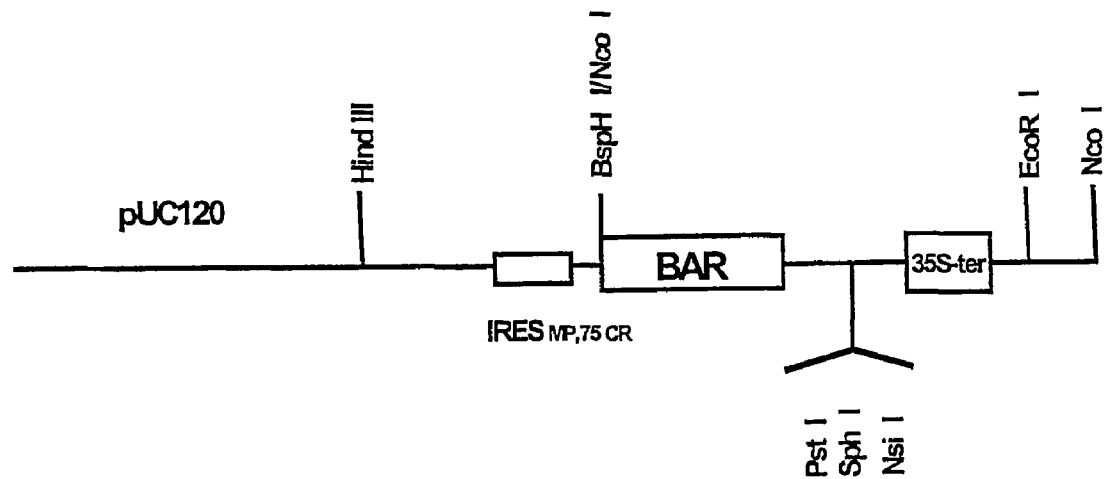

FIG. 2 depicts vector pIC1301 containing $IRES_{MP,75}^{CR}$, BAR and the 35S terminator.

Figure 3:
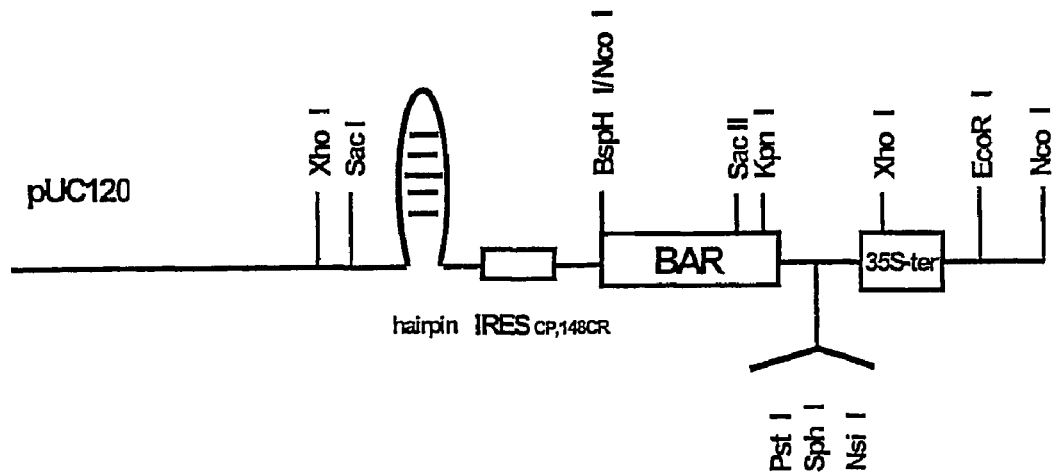

FIG. 3 depicts vector pIC1521 containing a "hairpin", $IRES_{CP,148}^{CR}$, BAR and the 35S terminator. The "hairpin" structure serves as an alternative to the translation stop codon, preventing the formation of the translational fusion products.

Figure 4:
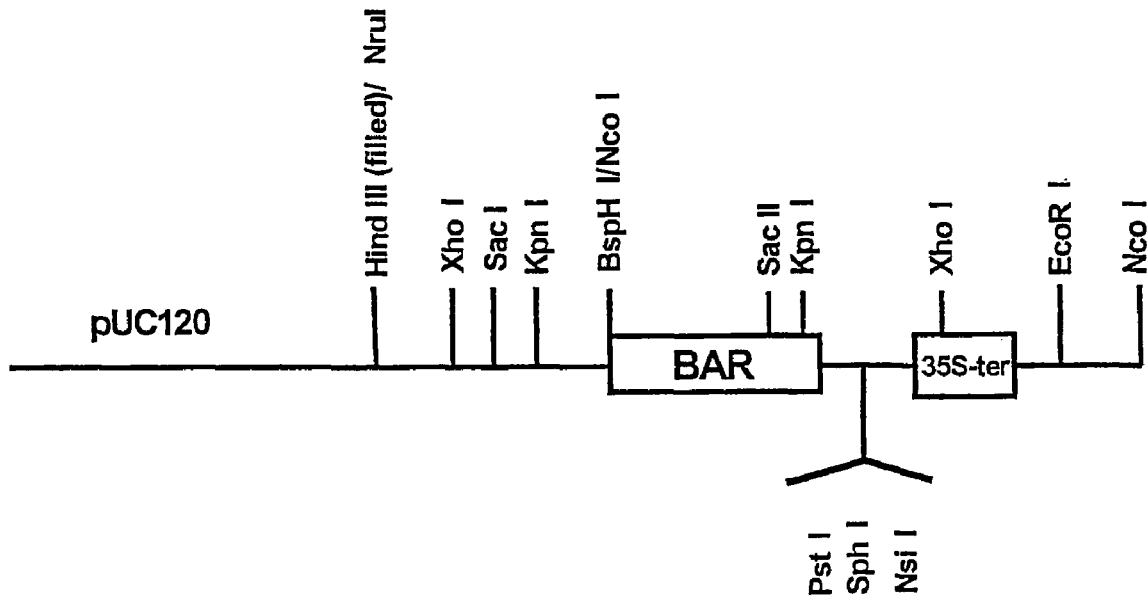

FIG. 4 depicts vector pIC1451 containing a promoterless BAR gene and the 35S terminator.

Figure 5:
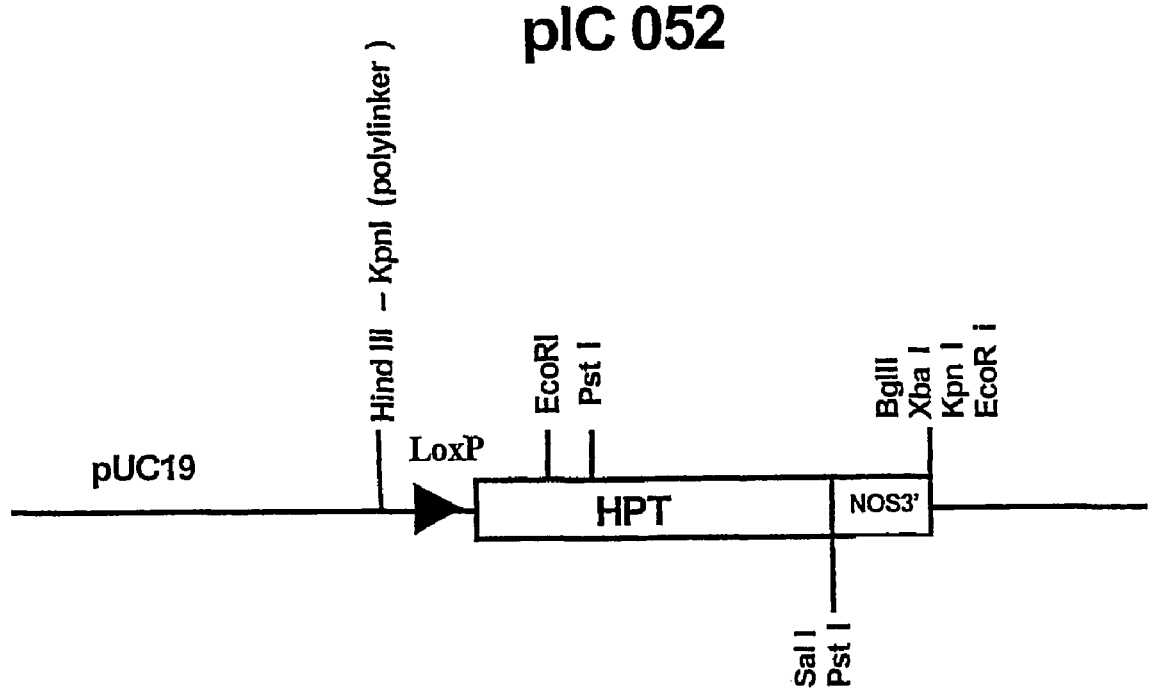

FIG. 5 depicts vector pIC052 containing loxP, HPT and nos terminator.

Figure 6:
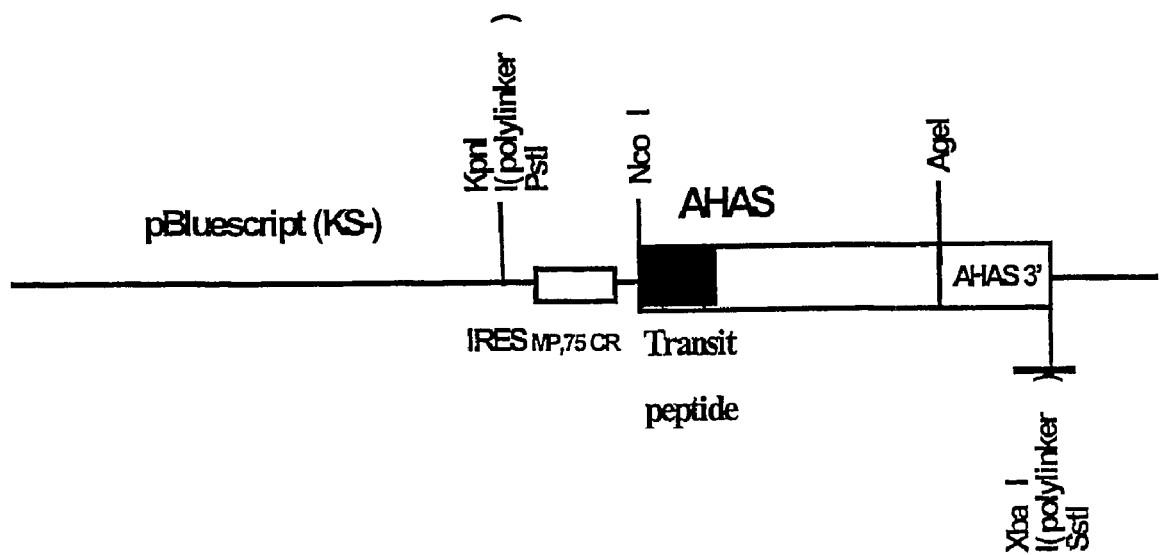

FIG. 6 depicts vector pIC06-IRES containing $IRES_{MP,75}^{CR}$, the AHAS gene, whereby AHAS is the mutated version of the *Arabidopsis* acetohydroxyacid synthase gene conferring resistance to imidazoline herbicides.

Figure 7:
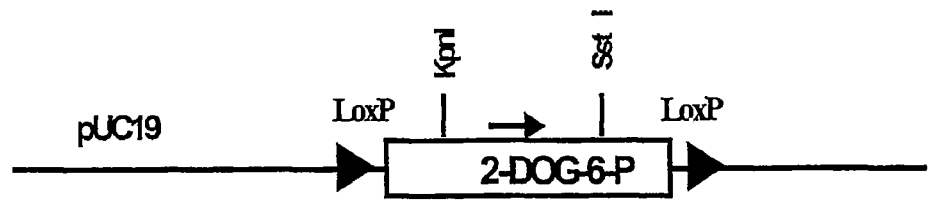
Figure 7:
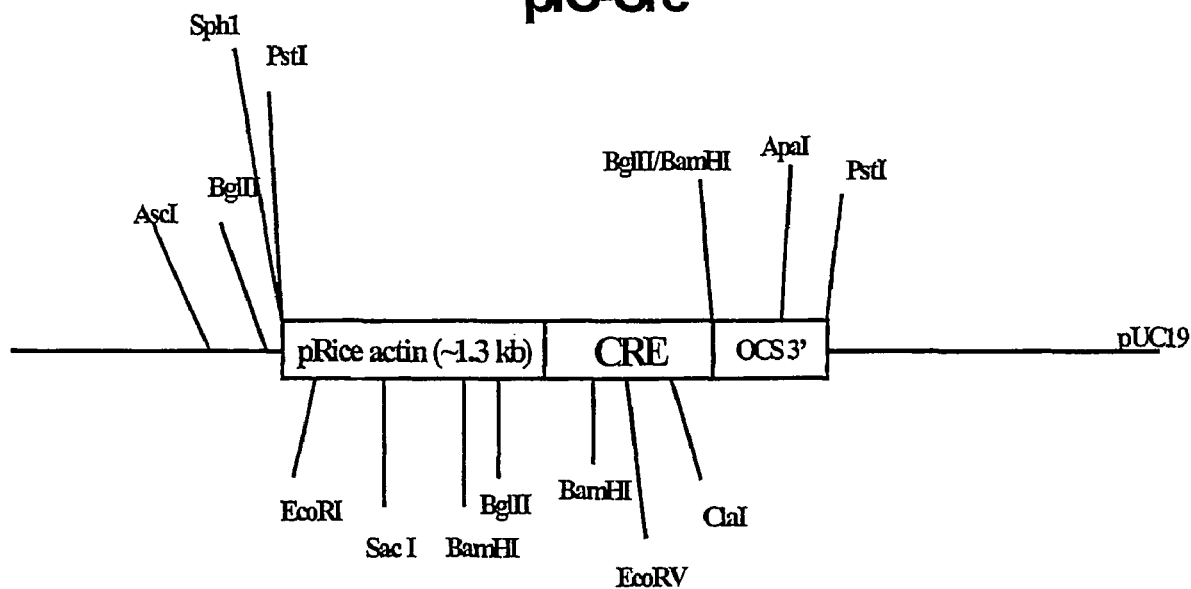

FIG. 7 depicts vectors pIC-DOG and pIC-CRE containing the coding sequence of the yeast 2-deoxyglucose-6-phosphate (2-DOG-6-P) phosphatase and cre recombinase under the control of the rice actin promoter, respectively.

Figure 8:
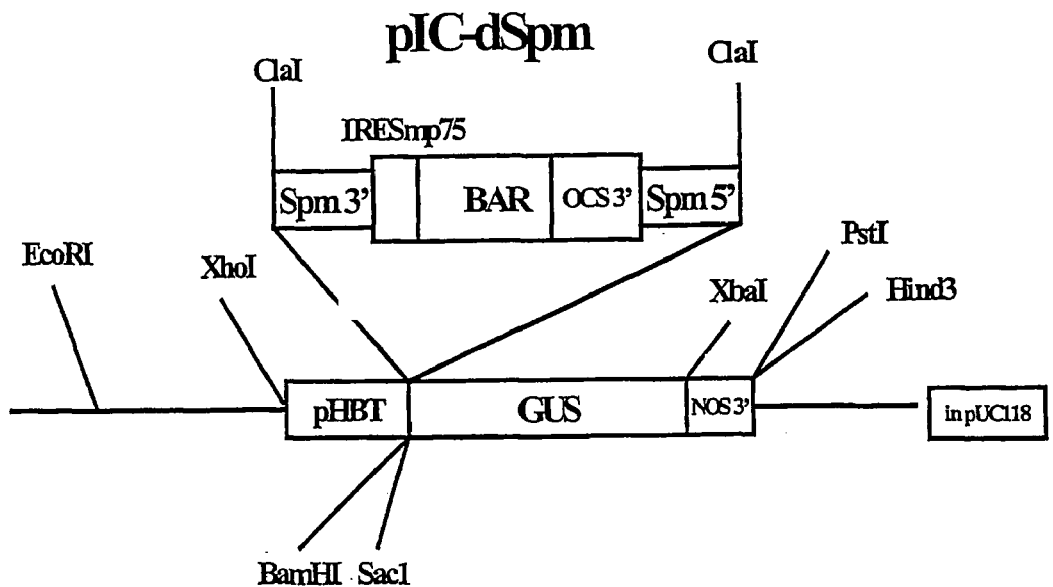
Figure 8:

FIG. 8 depicts the transposon-incorporated translational vector pIC-dSpm and vector pIC1491 containing a transposase. PHBT is a chimaeric promoter consisting of p35S enhancers fused to the basal part of the wheat C4PPDK gene.

Figure 9:
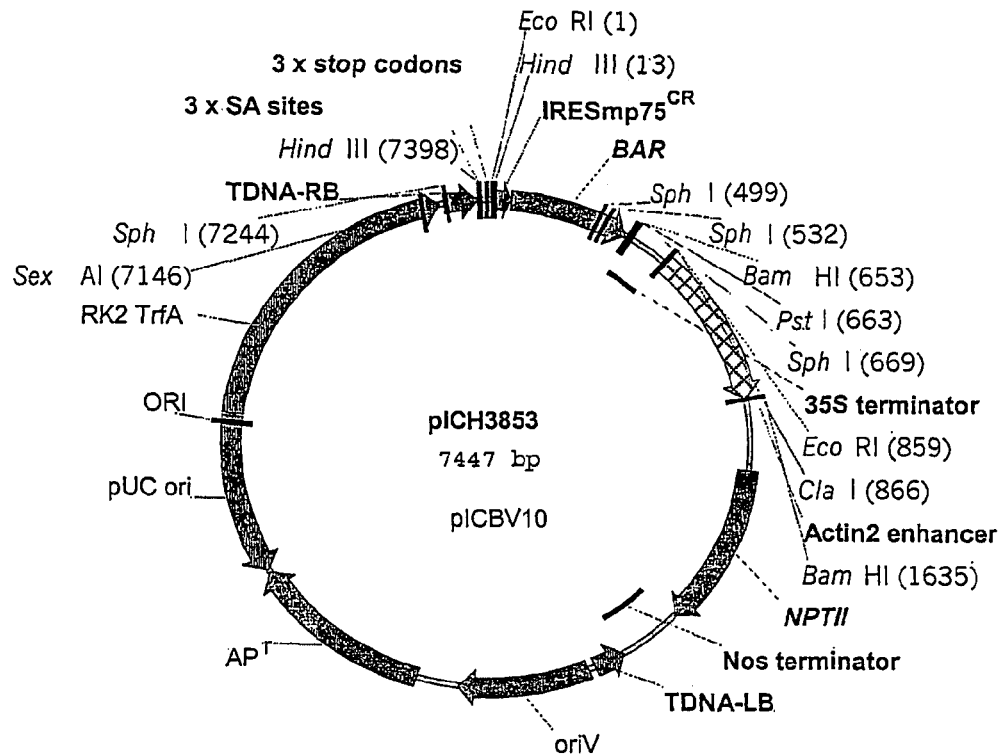
Figure 9:
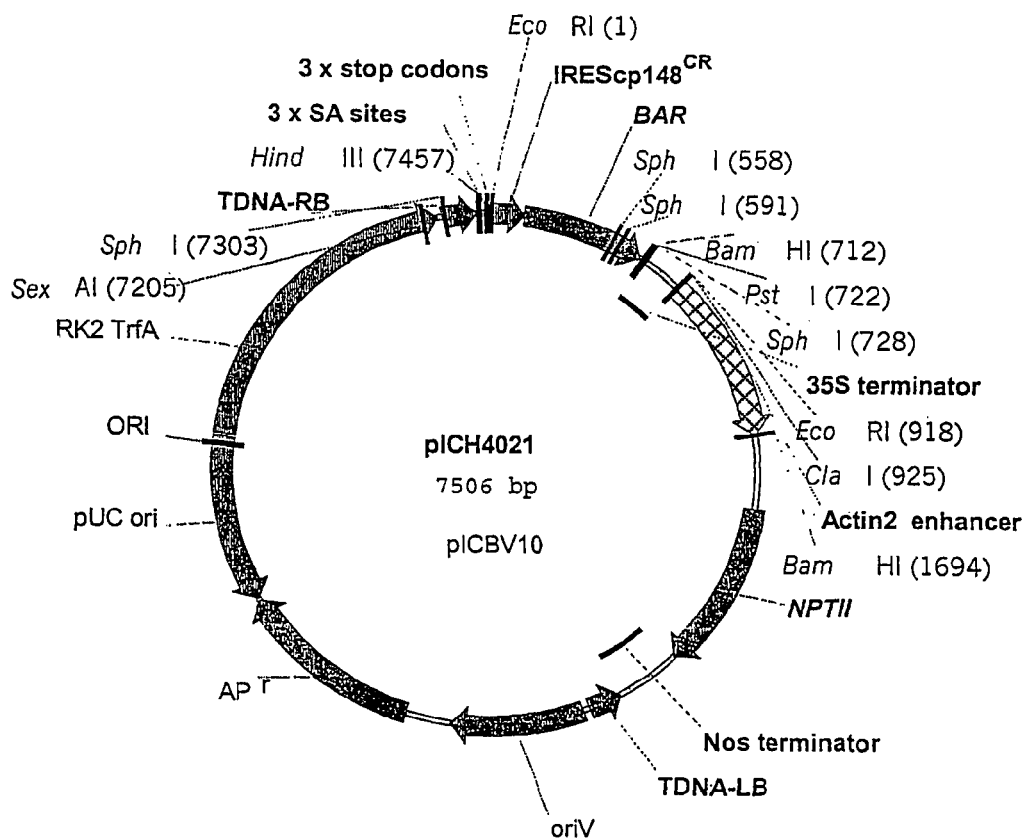
Figure 9:
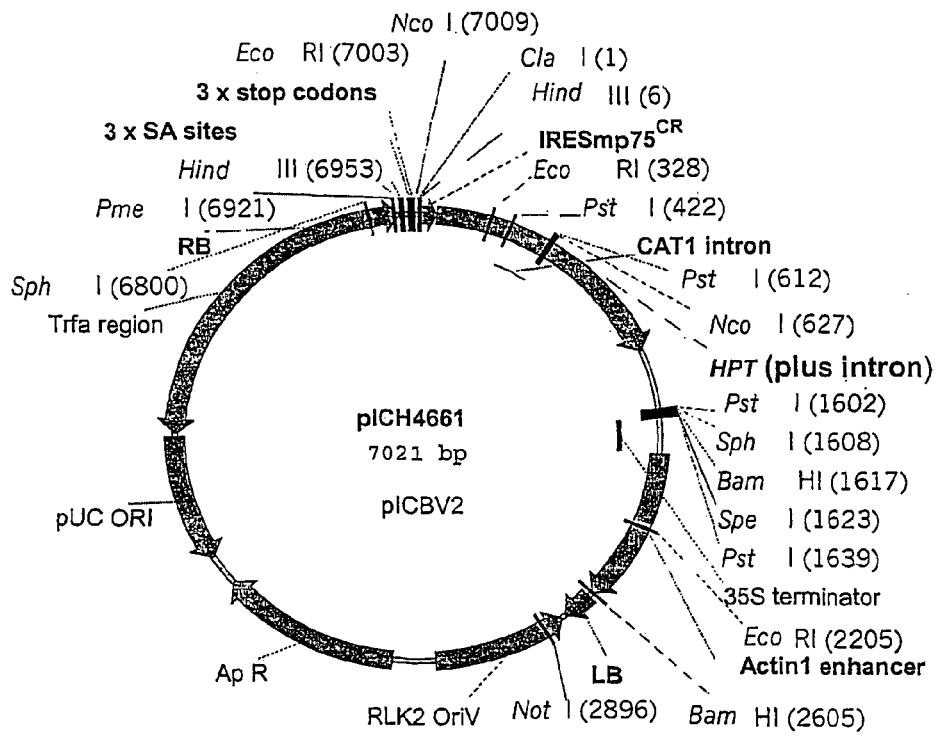
Figure 9:
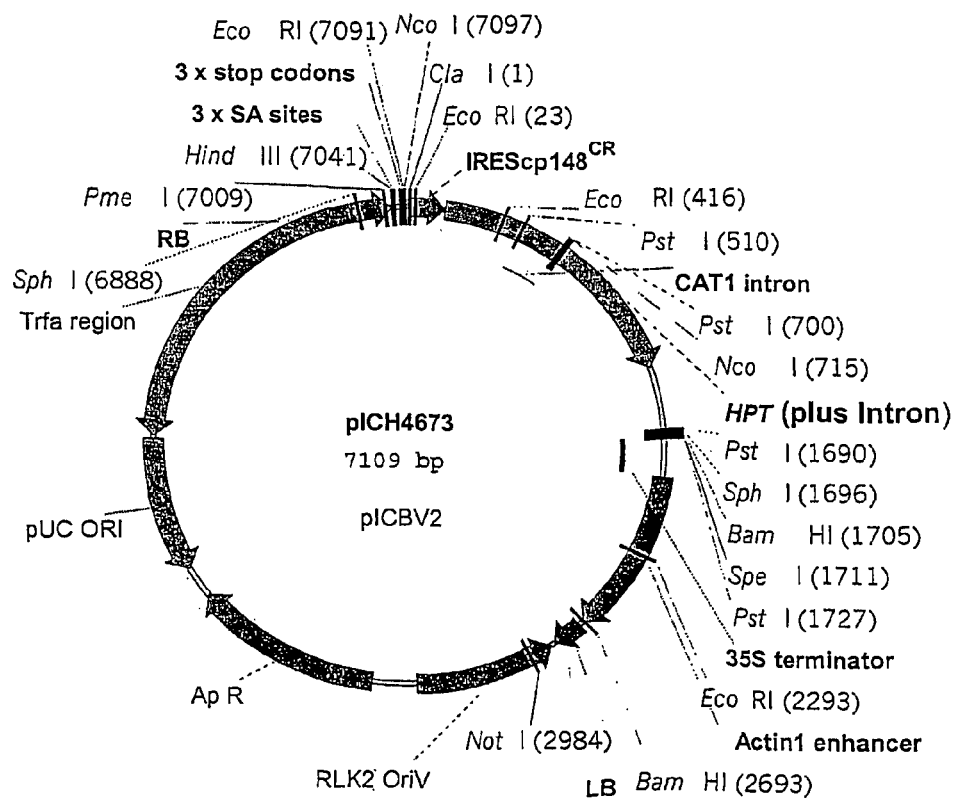

FIG. 9 depicts T-DNA based translational vectors.

A—the vectors contain the BAR gene under the control of IRESmp$^{75}$ (pICH3853) and IREScp$^{148}$ (pICH4021), respectively;

B—the vectors contain the HPT gene under the control of IRESmp$^{75}$ (pICH4661) and IREScp$^{148}$ (pICH4673), respectively.

SA stands for a splice acceptor site.

Figure 10:
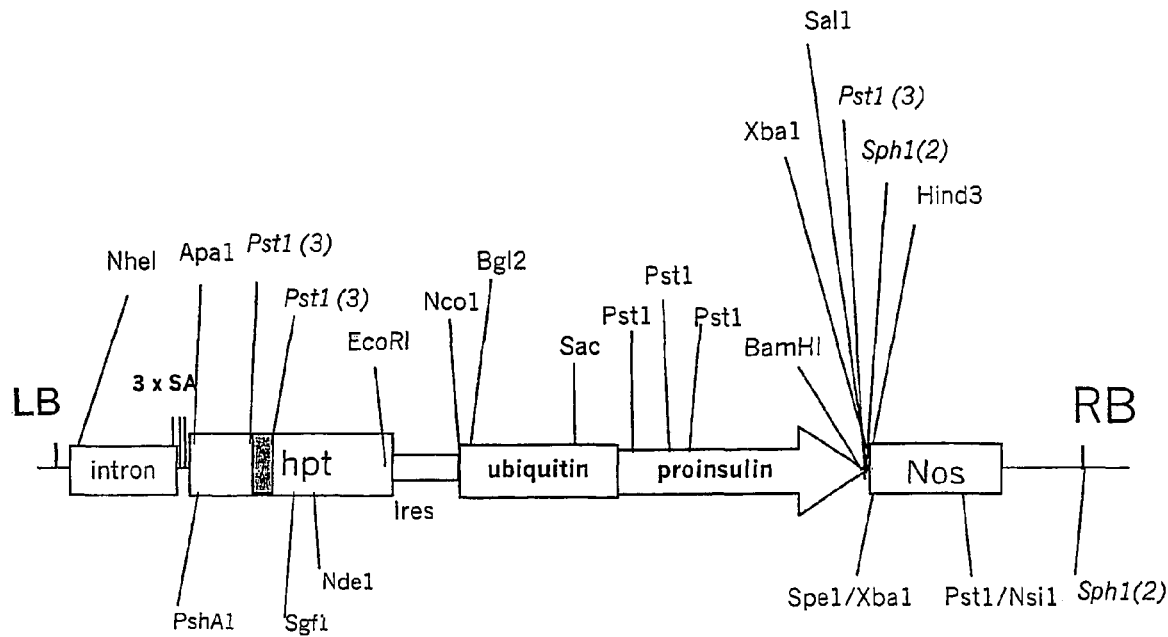
Figure 10:
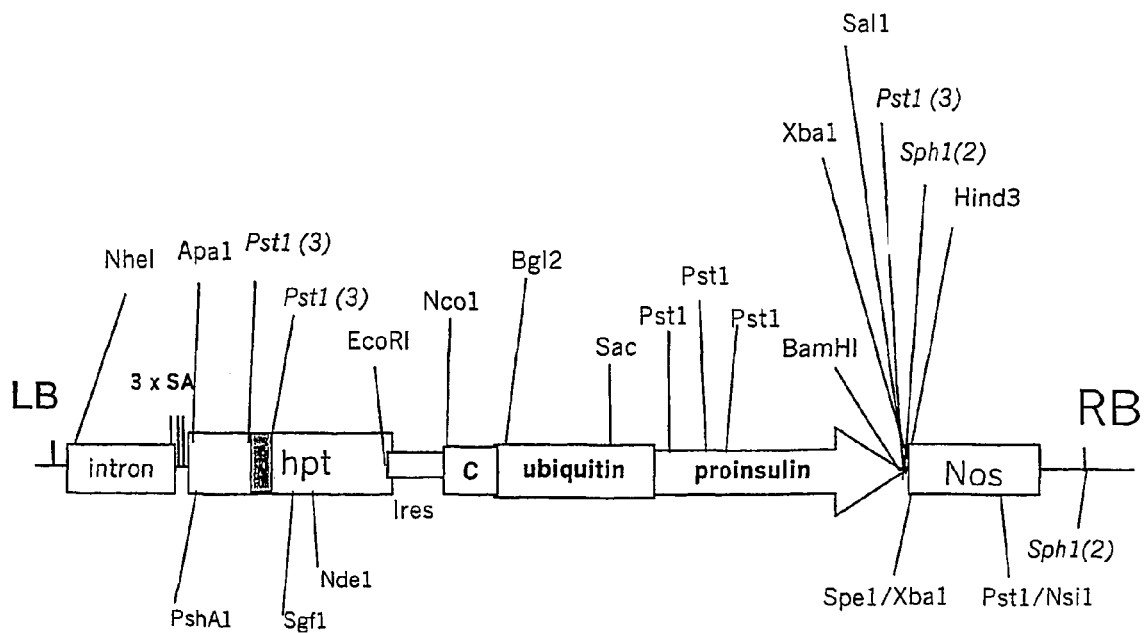

FIG. 10 depicts T-DNA based translational vectors pICH5410-UPI and pICH5410-CUPI designed to express proinsulin in plants. LB: left border, RB: right border.

SA stands for a splice acceptor site; C denotes the tobacco calreticulin signal peptide.

Figure 11:
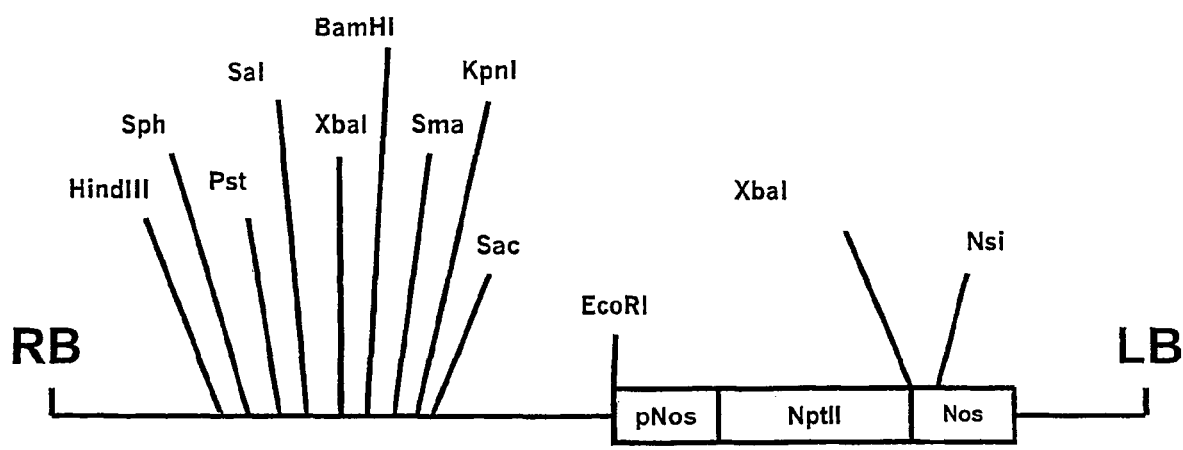
Figure 11:

FIG. 11 depicts binary vectors pICBV10 and pICBV2 (Example 9).

Figure 12:
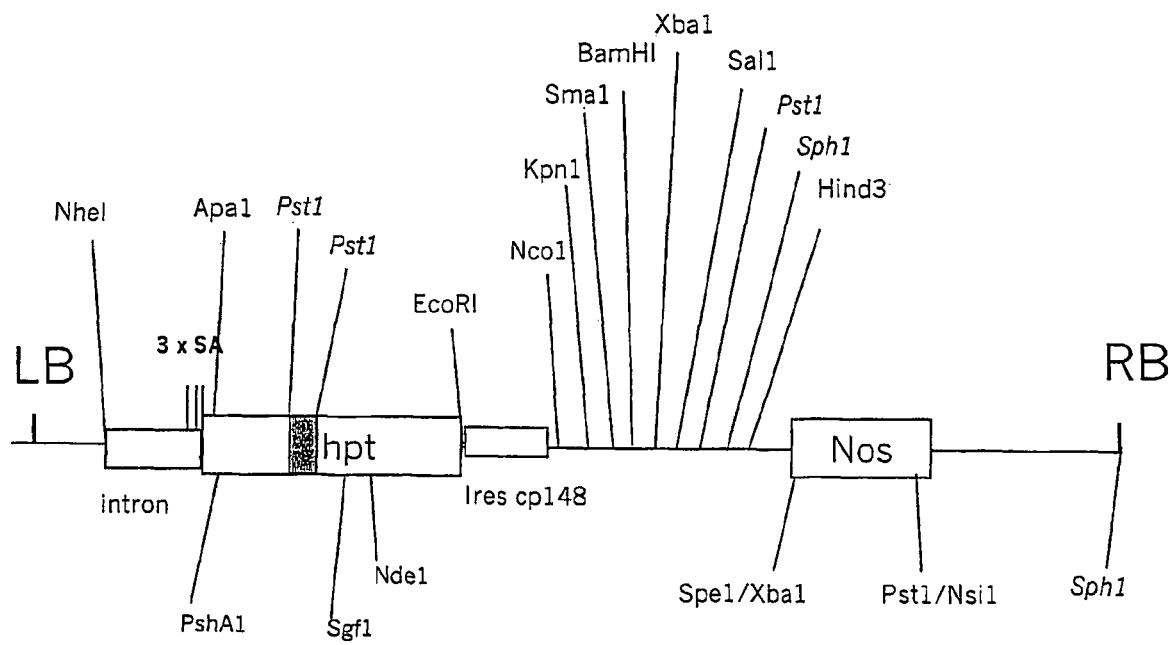

FIG. 12 depicts binary vector pICH5410 (Example 10).

DETAILED DESCRIPTION OF THE INVENTION

A primary objective of this invention is to provide a novel process or vector to produce transgenic plants for the stable expression of transgenic material integrated into a plant genome.

This object is achieved by a process for producing transgenic plants or plant cells capable of expressing a transgenic coding sequence of interest under transcriptional control of a host nuclear promoter by introducing into the nuclear genome a vector comprising in its transcript a sequence for binding a plant cytoplasmic ribosome in a form functional for initiation of translation and, downstream thereof, said transgenic coding sequence, and subsequently selecting plant cells or plants expressing said transgenic coding sequence. The gene of interest is under control of a translation signal, such as but not limited to, an IRES element, and the vector has no promoter operably linked to it. Such vectors rely on transgene insertions into transcriptionally active DNA of the host genome.

Further, a novel vector is provided for transforming plant cells, comprising, optionally after processing in the host cell, in its transcript a sequence for binding a plant cytoplasmic ribosome in a form functional for the initiation of translation and, downstream thereof, a coding sequence, said vector being devoid of a promoter functional for the transcription of said coding sequence.

Preferred embodiments are defined in the subclaims.

Construction of vectors for stable transformation of plants has been described by numerous authors (for review, see Hansen & Wright, 1999, *Trends in Plant Science*, 4, 226-231; Gelvin, S. B., 1998, *Curr: Opin. Biotech.*, 9, 227-232). The basic principle of all these constructs is identical—a fully functional transcription unit consisting of, in 5' to 3'direction, a plant-specific promoter, a structural part of a gene of interest and a transcriptional terminator, has to be introduced into the plant cell and stably integrated into the genome in order to achieve expression of a gene of interest.

We have developed a different technology for obtaining stable nuclear transformants of plants. Our invention relies on the surprising finding that the host plant transcription machinery is able to drive the formation of mRNA from a transgene of interest in a transformed plant cell. The proposed process utilizes vectors having a gene of interest that is not operationally linked to a promoter in said vector. Rather, they comprise the coding region of a gene of interest under the control of translation elements only. Said translational element may be a sequence for binding, preferably after transcription, a plant cytoplasmic ribosome thus enabling translation of a coding sequence downstream thereof. Preferably, said translational element is a ribosome entry site functional in plants and more preferably a plant-specific IRES element, notably an IRES element of plant viral origin, of plant origin, of non-plant origin or an artificially designed IRES element.

Such a vector DNA, after integration into the transcribed region of a resident plant gene, yields chimaeric mRNA and is subsequently translated into the protein of interest via initiation of translation from said sequence for binding a plant cytoplasmic ribosome (FIG. 1). To the best of our knowledge, there is no prior art concerning this approach for generating stable nuclear plant transformants. All prior art of using gene trap/enhancer trap vectors in plants focused on functional genomics tasks, e.g. on the identification and isolation of plant coding sequences and regulatory elements. Introduction and expression of new useful traits was not addressed.

It was very surprising, that, given the low proportion of transcriptionally active DNA in most plant genomes, transformation experiments utilizing translation vectors described in the present invention, yielded numerous transformants expressing the gene of interest. This was observed for both Agrobacterium-mediated and direct DNA delivery into the plant cells.

Our invention addresses imminent problems of reliable transgene expression. The transgene integrated into host genome using our invented process, relies on the transcription machinery including all or most of the transcriptional regulatory elements of the host's resident gene, thus minimizing transgene silencing usually triggered by xenogenetic DNA elements. The IRES elements contemplated in this invention are much shorter heterologous elements than promoters; in many cases, a plant-derived IRES may be used.

The vectors for transgene delivery can be built in many different ways. The simplest versions consist only of the coding region of a gene of interest or a portion thereof with a translation signal (basic translational vector). In a preferred vector, a translational stop signal is provided upstream of said sequences for binding a plant cytoplasmic ribosome. The stop signal may for example be at least one stop codon and/or an RNA hairpin secondary structure or the like. This stop signal causes abortion of upstream translation. More advanced versions may include a plant-specific IRES element followed by the coding region (of a gene) of interest. Advanced versions of the translational vector may include sequences for site-specific recombination (for review, see Corman & Bullock, 2000, *Curr Opin Biotechnol*, 11, 455-460) allowing either the subsequent replacement of an existing transgene or integration of any additional gene of interest into the transcribed region of the host DNA. Site-specific recombinases/integrases from bacteriophages and yeasts are widely used for manipulating DNA in vitro and in plants. Examples for recombinase-recombination site for the use in this invention include the following: cre recombinase-LoxP recombination site, FLP recombinase-FRT recombination sites, R recombinase-RS recombination sites, phiC31 integrase-attP/attB recombination sites etc.

The introduction of splicing sites into the translation vector may be used to increase the probability of transgene incorporation into the processed transcript.

The vector may further comprise a sequence coding for a targeting signal peptide between said sequence for binding a plant cytoplasmic ribosome and said coding sequence. Preferable examples of such signal peptides include a plastid transit peptide, a mitochondrial transit peptide, a nuclear targeting signal peptide, a vacuole targeting peptide, and a secretion signal peptide.

Various methods can be used to deliver translational vectors into plant cells, including direct introduction of said vector into a plant cell by means of microprojectile bombardment, electroporation or PEG-mediated treatment of protoplasts. Agrobacterium-mediated plant transformation also presents an efficient and preferred way of the translational vector delivery. The T-DNA insertional mutagenesis in Arabidopsis and Nicotiana with the promoterless reporter APH (3')II gene closely linked to the right T-DNA border showed that at least 30% of all inserts induced transcriptional and translational gene fusions (Koncz et al., 1989, *Proc. Natl. Acad. Sci.*, 86, 8467-8471).

A translational vector can also be cloned into transposable elements, facilitating the search for suitable transcribed regions and providing either a constitutive or tissue/organ-specific pattern of transgene expression. Transposable elements are extensively used in plants with the purpose of inactivation-based gene tagging (Pereira & Aarts, 1998, *Methods Mol Biol.*, 82, 329-338; Long & Coupland, 82, 315-328; Martin G B., 1998, *Curr Opin Biotechnol.*, 9, 220-226). Different versions of the transposon-tagging systems were developed. In the simplest version, transposons are used for insertional mutagenesis without any modifications except, possibly, for deletions or frame-shift mutations in order to generate non-autonomous transposable elements. In more sophisticated versions, additional genes are inserted into the transposable elements, e.g. reinsertion markers, reporter genes, plasmid-rescue vectors (Carroll et al., 1995, *Genetics*, 13, 407-420; Tissier et al., 1999, *Plant Cell*, 11, 1841-1852). There are so-called enhancer-trap and gene-trap systems (Sundaresan et al., 1995, *Genes Dev.*, 9, 1797-810; Fedorov & Smith, 1993, *Plant J.*, 3, 273-89). Transposable elements in such systems are equipped either with a promoterless reporter gene or a reporter gene under the control of a minimal promoter. In the first case, the reporter gene can be expressed following insertion into the transcribed region of host DNA just after the host promoter or insertion into the coding region of the host gene and creation of "in frame" fusion with the host gene transcript.

The chance for successful "in frame" fusion can be significantly increased by placing in front of the reporter gene a set of splicing donor and acceptor sites for all three reading frames (Nussaume et al., 1995, *Mol Gen Genet.*, 249, 91-101). In the second case, transcription of a reporter gene will be activated from the minimal promoter following insertion near the active host promoter (Klimyuk et al., 1995, *Mol Gen Genet.*, 249, 357-65). The success of such approaches for transposon tagging favors the use of a similar approach for the translational vectors with IRES elements in front of the gene of interest.

All approaches described above aim at designing a system that places a transgene under expression control of the resident gene in which the insertion occurred. This might be advantageous for specific tasks and cases. In many other cases, a modified pattern of transgene expression might be preferable. For such purposes, the translational vector can be equipped with transcriptionally active elements, such as enhancers or matrix/scaffold attachment regions (MARs) (for review see Allen G. C. et al., 2000, *Plant Mol Biol.*, 43, 361-376) or insulator elements (Geyer P K, 1997, *Curr. Opin. Genet. Dev.*, 2, 242-248; Nagaya et al., 2001, *Mol. Genet Genomics*, 265, 405-413), which can modulate the expression pattern of a transgene. When MARs or insulator elements are positioned on either side of a transgene their presence usually results in higher and more stable expression in transgenic plants or cell lines. It is also known that enhancer sequences can affect the strength of promoters located as far as several thousand base pairs away (Müller, J., 2000, *Current Biology*, 10, R241-R244). The feasibility of such an approach was demonstrated in experiments with activation tagging in *Arabidopsis* (Weigel et al., 2000, *Plant Physiol.*, 122, 1003-1013), where T-DNA-located 35S enhancer elements changed the expression pattern of resident genes, and in enhancer-trap transposon tagging described above. In the latter example, resident gene enhancers determined the expression pattern of the reporter transgene. This approach might be useful, for example, at the initial stages of plant transformation, or when modulation of the transgene expression pattern is required after the transformation. The enhancer sequences can be easily manipulated by means of sequence-specific recombination systems (inserted, replaced or removed) depending on the needs of the application. All these approaches are contemplated as useful components of the present invention.

Our approach was to preferably make a set of constructs based on different IRES elements functional in plant cells. The constructs contain IRES elements followed by a plant selectable marker gene and a transcription/translation termination signal. These constructs can be used directly for plant cell transformation after being linearized from the 5' end in front of the IRES sequences or can be cloned into the T-DNA for Agrobacterium-mediated DNA transfer. Another set of constructs, serving as controls, contained either a promoterless selectable gene (a negative control) or a selectable gene under the control of a constitutive promoter functional in monocot and/or dicot cells (a positive control). DNA was transformed into plant cells using different suitable technologies, such as Ti-plasmid vector carried by *Agrobacterium* (U.S. Pat. Nos. 5,591,616; 4,940,838; 5,464,763), particle or microprojectile bombardment (U.S. Pat. No. 5,100,792; EP 00444882 B1; EP 00434616 B1). In principle, other plant transformation methods could be used, such as but not limited to, microinjection (WO 09209696; WO 09400583 A1; EP 175966 B1), electroporation (EP 00564595 B1; EP 00290395 B1; WO 08706614 A1).

The transformation method depends on the plant species to be transformed. Our exemplification includes data on the transformation efficiency for representatives of monocot (e.g. *Triticum monococcum, Pennisetum glaucum*) and dicot (e.g. *Brassica napus, Orichophragmus violaceous, Arabidopsis thaliana, Nicotiana tabacum*) plant species, thus demonstrating the feasibility of our approach for plant species of different phylogenetic origin and with different densities and organization of transcribed regions within a species' genome.

The transgenic coding sequence in the vector may represent only part of a gene of interest, which gene is reconstructed to a functional length as a result of site-directed or homologous recombination or other specific recombination processes. The translation of the sequence of interest is preferably cap-independent. The host may be modified for inhibiting (or enhancing) cap-dependent translation or for enhancing (or inhibiting) cap-independent translation. This may be accomplished by treatment with exogenous agents or by including a sequence in the vector or said plant, which expression has the desired effect.

In one embodiment of our invention we demonstrate the transformation of monocot and dicot species using translational vectors. We have found that the frequency of transformation with direct DNA delivery (microprojectile bombardment, PEG-mediated protoplasts transformation) can be approximately 1-5% of that of a transcriptional vector depending on the plant species involved. This is usually lower for plants with large genomes and a high proportion of non-coding, repetitive sequences, e.g. monocots (*Triticum monococcum, Pennisetum glaucum*), than for plants with smaller genomes rich in coding regions (*O. violaceous, Brassica napus, N. tabacum*). Use of an Agrobacterium-mediated transformation protocol provides higher efficiency of transgene delivery into different plant species and the transformation frequency of a translational vector can vary roughly in the range of 3-10% to that of a transcriptional vector. It is important to mention here that the transformation frequency is not a limiting factor in genetic engineering technology. Therefore, these comparably low frequencies do not affect in any way neither the efficiency of plant genetic transformation nor the duration of the process.

Our invention may be used to introduce useful traits into plants, in particular in order to improve resistance against abiotic (salt-, cold-, drought-, photooxydative stress tolerance) and biotic (pathogen resistance) stresses, modify metabolism, increase yield, improve quality of food etc. Translational vectors are especially well suited for such purposes, as they provide the necessary flexibility for obtaining a required expression pattern. The approach is of extreme value for functional genomics, as it provides the much needed flexibility and sophistication to the currently existing very limited set of gene expression systems, which are restricted to the use of a few constitutive, tissue- and organspecific and inducible promoters. These promoters represent only a tiny fraction of regulatory elements existing in planta and do not present an adequate choice for many different applications. Translational vectors with useful traits can be used directly for the purpose of obtaining transgenic plants with required phenotypic features and/or for identifying the plant regulatory elements necessary to provide such features by regulating the expression pattern of said useful trait. This approach is strategically different from existing enhancer-trap technology, that allows only the identification of regulatory elements with the help of reporter genes, but not the evaluation of the in situ usefulness of such elements for regulating the expression of a gene of interest.

The genes of interest, or fragments thereof, that can be introduced, in sense or antisense orientation, using our invention, include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof, isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polyopeptide toxin, protoxin etc.), insect specific toxin AalT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, Brassica AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Plants can be engineered using our invention for the purpose of molecular farming of commercially valuable or pharmaceutically important proteins. In another embodiment of this invention we describe the expression of proinsulin as ubiquitin-proinsulin or as calreticulin signal peptide-ubiquitin-proinsulin fusion (FIG. 10). Ubiquitin (UBQ) fusions allow to produce the protein of interest with any first N-terminal amino acid residue including methionin in eukaryotic cells, as these fusions are rapidly and precisely processed in vivo to release the fused protein moieties in free forms (Hondred et al., 1999, *Plant Physiol.*, 119, 713-724). Also the synthesis of a protein as a UBQ fusion can significantly increase its accumulation.

Any human or animal protein can be expressed using a translational vector. Examples of such proteins of interest include inter alia immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The process of the invention may further comprise introducing a gene encoding a post-transcriptional gene silencing (PTGS) suppressor protein or a function-conservative variant or fragment thereof into a plant for suppressing PTGS of said transgenic coding sequence. Said PTGS suppressor protein gene or function-conservative variant or fragment thereof may be provided to a plant on the same vector carrying said transgenic coding sequence or on an extra vector. Said PTGS suppressor protein gene may be expressed under translational control of a sequence for binding a plant cytoplasmic ribosome. Alternatively, it may be expressed under transcriptional control of a promoter. Said PTGS suppressor protein is preferably of viral or plant origin. Examples of PTGS suppressor proteins are potato virus X p25 protein, african cassaya mosaic virus AC2 protein, rice yellow mottle virus P1 protein, tomato bushy stunt virus 19K protein, rgs CAM or a function-conservative variant or fragment of one of these proteins. Said function-conservative variant or fragment preferably has a sequence identity of 75% to one of the above protein. Details on PTGS suppressor proteins and their use can be found in WO0138512.

Using our invention, the transgene of interest can be expressed together with a selectable/scorable marker from the same transcript, thus allowing for the direct selection of the best recombinant protein producer. Examples of such selectable/scorable markers include inter alia genes or fragments of: neomycin phosphotransferase II (NPTII), hygromycin phosphotransferase, aminoglycoside 6'-N-acetyltransferase, 5-enolpyruvylshikimate-3-phosphate synthase, phosphinothricin acetyl transferase (BAR), betaine aldehyde dehydrogenase (BADH), dihydrofolate reductase (DFR1), 6' gentamicin acetyltransferase (6' GAT), acetolactate synthase (ALS), phosphomannose-isomerase (PMI), glyphosate oxidoreductase, acetohydroxyacid synthase (AHAS), 2-deoxy-glucose-6-phosphate phosphatase (2-DOG-6-P), luciferase, green fluorescent protein (GFP), and selectable and screenable marker genes fusions. Optionally, the selectable marker can be linked with a counter-selectable marker (e.g. bacterial codA gene encoding cytosine deaminase or bacterial cytochrome P450 mono-oxygenase gene, etc) and can be flanked by recombination sites recognized by (a) site-specific recombinase(s). This allows the removal of the selectable marker when desired and facilitates the screening for such events.

Any plant species with established transformation protocols can be routinely transformed using the translational vector approach described herein, including woody species like poplar and conifers, agriculturally important crops like cotton, *Brassica*, as well as decorative plant species, like *Chrysanthemum*, etc.

EXAMPLES

Example 1

Construction of IRES Containing Vectors

Series of IRES-mediated expression vectors were constructed using standard molecular biology techniques (Maniatis et al., 1982, Molecular cloning: a Laboratory Manual. Cold Spring Harbor Laboratory, New York). Vector pIC1301 (FIG. 2) was made by digesting plasmid pIC501 (p35S-GFP-IRES$_{MP,75}^{CR}$-BAR-35S terminator in pUC120) with HindIII and religating large gel-purified fragment. The IRES$_{MP,75}^{CR}$ sequence represents the 3' terminal 75 bases of the 5'-non-translated leader sequence of the subgenomic RNA of the movement protein (MP) of a crucifer (CR)-infecting tobamovirus.

Vector pIC1521 (FIG. 3) was made following three steps of cloning. In the first step, pIC1311 was constructed by ligating the large HindIII-PstI fragment of pIC031 with the small HindIII-NcoI fragment of pIC032 and the small BspHI-PstI fragment of pIC018. The resulting construct pIC1311 (not shown) containing the BAR gene under the control of the 35S promoter was used as the comparative control in the transformation experiments. Plasmid pIC1311 was digested with HindIII-NruI and blunt-ended by treatment with Klenow fragment of DNA polymerase I. The large restriction fragment was gel-purified and religated producing pIC1451 (promoterless BAR-35S terminator; see FIG. 4). Ligation of the large Sac1-Pst1 fragment of pIC1451 with the small SacI-NcoI fragment of pIC033 and the small BspHI-PstI fragment of pIC018 produced pIC1521 (FIG. 3). This construct contains a "hairpin" in front of the IRES$_{cp,148}^{CR}$ (CP stands for coat protein) element. The hairpin structure is formed by the presence of an inverted tandem repeat formed by KpnI-EcoRI and ClaI-KpnI fragments from the Bluescript II SK+ polylinker sequence.

All vectors were linearized for use in the transformation experiments by digesting either with SacI (pIC1521; pIC1451) or HindIII (pIC1311; pIC1301) restriction enzyme and gel-purified to separate from undigested vectors.

Example 2

PEG-mediated Protoplast Transformation of *Brassica napus*

Isolation of Protoplasts

The isolation of *Brassica* protoplasts was based on previously described protocols (Glimelius K., 1984, *Physiol. Plant*, 61, 38-44; Sundberg & Glimelius, 1986, *Plant Science*, 43, 155-162 and Sundberg et al., 1987, *Theor. Appl. Genet.*, 75, 96-104).

Sterilized seeds (see Appendix) were germinated in 90 mm Petri dishes containing ½ MS medium with 0.3% Gelrite. The seeds were placed in rows slightly separated from each other. The Petri dishes were sealed, tilted at an angle of 45° and kept in the dark for 6 days at 28° C. The hypocotyls were cut into 1-3 mm long pieces with a sharp razor blade. The blades were often replaced to avoid the maceration of the material. The pieces of hypocotyls were placed into the TVL solution (see Appendix) to plasmolise the cells. The material was treated for 1-3 hours at room temperature. This pre-treatment significantly improves the yield of intact protoplasts. The preplasmolysis solution was replaced with 8-10 ml of enzyme solution (see Appendix). The enzyme solution should cover all the material but should not to be used in excess. The material was incubated at 20-25° C. in dark for at least 15 hours. The Petri dishes were kept on a rotary shaker with very gentle agitation.

The mixture of protoplasts and cellular debris was filtered through 70 mm mesh size filter. The Petri dishes were rinsed with 5-10 ml of W5 solution (Menczel et al., 1981, Theor. Appl. Genet., 59, 191-195) (also see Appendix) that was also filtered and combined with the rest of the suspension. The protoplast suspension was transferred to 40 ml sterile Falcon tubes and the protoplasts were pelleted by centrifugation at 120 g for 7 min. The supernatant was removed and the pellet of protoplasts was re-suspended in 0.5 M sucrose. The suspension was placed into 10 ml sterile centrifuge tubes (8 ml per tube) and loaded with 2 ml of W5 solution. After 10 min of centrifugation at 190 g the intact protoplasts were collected from the interphase with a Pasteur pipette. They were transferred to new centrifuge tubes, resuspended in 0.5 M mannitol with 10 mM $CaCl_2$ and pelleted at 120 g for 5 min.

PEG Treatment

The protoplasts were resuspended in the transformation buffer (see Appendix). The protoplast concentration was determined using the counting chamber and then adjusted to $1-1.5 \times 10^6$ protoplasts/ml. The 100 μl drop of this suspension was placed at the lower edge of the tilted 6-cm Petri dish and left for a few minutes allowing the protoplasts to settle. The protoplasts were then gently mixed with 50-100 μl of DNA solution (Qiagen purified, dissolved in TE at the concentration 1 mg/ml). Then 200 μl of PEG solution (see Appendix) was added dropwise to the protoplasts/DNA mixture. After 15-30 min the transformation buffer (or W5 solution) was added in small aliquots (dropwise) until the dish was almost filled (~6 ml). The suspension was left to settle for 1-5 hours. Then the protoplasts were transferred to centrifuge tubes, re-suspended in W5 solution and pelleted at 120 g for 5-7 min.

Protoplast Culture and Selection for Transformants

The protoplasts were transferred to the culture media 8pM (Kao & Michayluk, 1975, *Planta*, 126, 105-110; also see the Appendix) and incubated at 25° C., low light density, in 2.5 cm or 5 cm Petri dishes with 0.5 ml or 1.5 ml of media, respectively. Protoplast density was $2.5 \times 10^4$ protoplasts/ml. The three volumes of fresh 8pM media without any hormones were added right after the first protoplasts division. The cells were incubated at high light intensity, 16 hours per day.

After 10-14 days the cells were transferred to K3 media (Nagy & Maliga, 1976, *Z. Pflanzenphysiol.*, 78, 453-455) with 0.1 M sucrose, 0.13% agarose, 5-15 mg/L of PPT and the hormone concentration four times less than in 8pM medium. To facilitate the transfer to fresh media, the cells were placed on the top of sterile filter paper by carefully spreading them in a thin layer. The cells were kept at high light intensity, 16 hours per day. The cell colonies were transferred to Petri dishes with differentiation media K3 after their size had reached about 0.5 cm in diameter.

Example 3

Transformation of *Triticum monococcum* by Microprojectile Bombardment

Plant Cell Culture

Suspension cell line of *T. monococcum L.* was grown in MS2 (MS salts (Murashige & Skoog, 1962 *Physiol. Plant.*, 15, 473-497), 0.5 mg/L Thiamine HCl, 100 mg/L inosit, 30 g/L sucrose, 200 mg/L Bacto-Tryptone, 2 mg/L 2,4-D) medium in 250 ml flasks on a gyrotary shaker at 160 rpm at 25° C. and was subcultured weekly. Four days after a subculture the cells were spread onto sterile 50 mm filter paper disks on a gelrite-solidified (4 g/L) MS2 with 0.5 M sucrose.

Microprojectile Bombardment

Microprojectile bombardment was performed utilizing the Biolistic PDS-1000/He Particle Delivery System (Bio-Rad). The cells were bombarded at 900-1100 psi, with 15 mm distance from a macrocarrier launch point to the stopping screen and 60 mm distance from the stopping screen to a target tissue. The distance between the rupture disk and a launch point of the macrocarrier was 12 mm. The cells were bombarded after 4 hours of osmotic pre-treatment.

A DNA-gold coating according to the original Bio-Rad's protocol (Sanford et al., 1993, In: Methods in Enzymology, ed. R. Wu, 217, 483-509) was done as follows: 25 µl of gold powder (0.6, 1.0 mm) in 50% glycerol (60 mg/ml) was mixed with 5 µl of plasmid DNA at 0.2 µg/µl, 25 µl $CaCl_2$ (2.5 M) and 10 µl of 0.1 M spermidine. The mixture was vortexed for 2 min followed by incubation for 30 min at room temperature, centrifugation (2000 rpm, 1 min), washing by 70% and 99.5% ethanol. Finally, the pellet was resuspended in 30 µl of 99.5% ethanol (6 µl/shot).

A new DNA-gold coating procedure (PEG/Mg) was performed as follows: 25 µl of gold suspension (60 mg/ml in 50% glycerol) was mixed with 5 µl of plasmid DNA in an Eppendorf tube and supplemented subsequently by 30 µl of 40% PEG in 1.0 M $MgCl_2$. The mixture was vortexed for 2 min and than incubated for 30 min at room temperature without mixing. After centrifugation (2000 rpm, 1 min) the pellet was washed twice with 1 ml of 70% ethanol, once by 1 ml of 99.5% ethanol and dispersed finally in 30 µl of 99.5% ethanol. Aliquots (6 µl) of DNA-gold suspension in ethanol were loaded onto macrocarrier disks and allowed to dry up for 5-10 min.

Plasmid DNA Preparation

Plasmids were transformed into *E. coli* strain DH10B, maxi preps were grown in LB medium and DNA was purified using the Qiagen kit.

Selection

For stable transformation experiments, the filters with the treated cells were transferred onto the solid MS2 medium with the appropriate filter-sterilized selective agent (150 mg/L hygromycin B (Duchefa); 10 mg/L bialaphos (Duchefa). The plates were incubated in the dark at 26° C.

Example 4

Transformation of *Orychophragmus violaceus* by Microprojectile Bombardment

Preparation of the suspension culture

Plants of *O. violaceus* are grown in vitro on MS medium, 0.3% Gelrite (alternatively, ½ MS, 2% sucrose and 0.8% agar) at 24° C. and 16/8 hours day/night photoperiod for 3-4 weeks. Four-six leaves (depending of size) were cut into small peaces and transferred to the Magenta box with 30 ml of Callus Inducing Medium (CIM) (see the Appendix). The material was kept for 4-5 weeks at dim light (or in dark) at 24° C. and vigorous agitation. During this period the fresh CIM media was added to keep the plant tissue in the Magenta box covered with liquid. The cells sticking to the wall of the Magenta box were released into the media by vigorous inverting and shaking of the box.

Preparation of Plant Material for Microprojectile Bombardment

The aliquote of cell suspension was carefully placed onto the sterile filter paper supported by solid CIM media in Petri dish. The Petri dish with plant material was kept in the dark for 5-7 days. Four hours before the procedure, the filter paper with cells was moved to fresh CIM with 10% sucrose. Microprojectile bombardment was performed as described in Example 3. Fourteen hours after the bombardment the material was transferred to CIM with 3% sucrose and kept in the dark.

Selection for Transformants

Two-four days after the bombardment, the filter paper with cells was transferred to the plate with CIM supplemented with the appropriate selection agent (10-15 µg/ml PPT). Every seven days the material was transferred to fresh selection media. The plates were kept in the dark and after approximately 6 weeks the plant material was transferred to the Petri plates with Morphogenesis Inducing Medium (MIM) (see the Appendix) supplemented with the appropriate selection agent (10-15 µg/ml PPT). The plates were incubated at high light intensity, 16 hours day length.

Example 5

Transformation of *Triticum monococcum* with Promoterless loxP-HPT Gene

The construct pIC052 (FIG. 6) was linearized by digestion with HindIII restriction enzyme, gel-purified to separate undigested material and used for the microprojectile bombardment as described above (see EXAMPLE 3). The linearized vector contains pUC19 polylinker (57 bp) followed by a loxP site from the 5' end of the HPT gene. In general, approximately 100 bp is located at the 5' end of translation start codon of HPT gene. Thirty four plates were transformed and after 1.5 months of selection on hygromycin-containing media (EXAMPLE 3), three hygromycin resistant colonies were recovered. The sequence of the integration sites recovered by IPCR, confirmed the independency of all three transformants.

Example 6

Transformation of Orychophragmus Leaves with Promoterless $IRES_{MP,75}^{CR}$-AHAS Plant acetohydroxyacid synthase (AHAS) is a nuclear encoded, chloroplast targeted protein which catalyses the first step in the biosynthesis of the branched chain amino acids. It is under allosteric control by these amino acids and can be inhibited by several classes of herbicides.

The construct pIC06-IRES was made by replacing the promoter of the *Arabidopsis* AHAS(Ser653-Asn) gene (1.3 Kb PstI-NcoI fragment) in pIC06 with the $IRES_{MP,75}^{CR}$ sequence. The final construct (FIG. 6) contained the mutated version of the Arabidopsis acetohydroxyacid synthase (AHAS) gene with a single amino acid substitution (Ser653Asn) conferring resistance to the imidazoline herbicide family (Sathasivan, Haughn & Murai, 1991, *Plant Physiol.*, 97, 1044-1050). The plasmid was linearized by treatment with SalI restriction enzyme and used for microprojectile bombardment of freshly induced *O. violaceous* suspension culture. Leaves of sterile *O. violaceous* plants were cut onto the small peaces and placed in the liquid High Auxin Medium (HAM) (see the Appendix) in Magenta boxes on a rotary shaker to induce suspension culture. After 7-14 days the suspension culture was transferred to the Petri dishes with Greening Medium (GM) covered by sterile filter paper (see the Appendix). After 3 days the filter paper with the cells was transferred on GM supplemented with 0.4 M sucrose. After four hours the cells were used for microprojectile bombardment with linearized DNA of pIC06-IRES, as described in EXAMPLE 3. After 14 hours the filter paper with cells was transferred to GM, 3% sucrose. Two days later the cells were transferred to GM with 0.7 µM imazethapyr (AC263, 499 or Pursuit, American Cyanamid). The cells were subcultured every 7-10 days. Putative events were identified after approximately four-six weeks and the transformants were selected under high light intensity, 16 hours per day, on the regeneration medium (RM) with 1-2 µM imazethapyr.

Example 7

Expression of 2-DOG-6-P Gene Using Translational Vector

The aim of this example is to demonstrate the possibility of manipulation with transgenic plant cells already containing translational vector sequences with the sequence-specific recombination sites.

The hygromycin-resistant *T. monococcum*-cells transformed with vector pIC052 (EXAMPLE 5) were used for microprojectile co-bombardment with two plasmids, pIC-DOG and pIC-CRE (FIG. 7). Plasmid pIC-DOG contains promoterless 2-deoxyglucose-6-phosphate (2-DOG-6-P) phosphatase cDNA (patent WO 98/45456) flanked by two loxP sites. Cre-mediated integration of the 2-DOG-6-P gene into the loxP site of pIC052-containing transformants leads to the expression of 2-DOG-6-P from a resident promoter. Such expression confers resistance to 2-deoxyglucose (2-DOG). The resistant colonies were selected as described in EXAMPLE 3, but using 0.075-0.1% of 2-DOG as the selective agent.

Example 8

Transposon-incorporated translational vector

The aim of this example is to show an alternative way to the direct transformation of directing translational vector to a desired transcriptional site in a host genome.

Co-transformation of *O. violaceous* cells with the constructs shown in FIG. 8 and selection for transformants was performed as described in EXAMPLE 4. The non-autonomous transposable dSpm element contains a promoterless BAR gene preceeded from its 5' end IRES$_{MP,75}^{CR}$. The transposition induced by Spm transposase facilitates the search for transcriptionally active regions with a desired expression pattern (in this case—constitutive) in said host genome, thus increasing the number of recovered primary transformants. Indeed, the number of transformants was 3-4 times higher than with the IRES$_{MP,75}^{CR}$-BAR gene alone (pIC1301, FIG. 2).

Example 9

T-DNA Based Translational Vectors

The aim of this example is to demonstrate an Agrobacterium-mediated delivery of translational vectors into plant cells.

The constructs pICH3853, pICH4021, pICH4661 and pICH4673 (FIG. 9A,B) were made on the basis of binary vectors pICBV10 and pICBV2 (see FIG. 11). Constructs pICH3853 and pICH4021 contain IRES-BAR preceded by three splice acceptor sites (SA) in order to facilitate the incorporation of the translational vector coding for BAR into transcripts. An identical strategy was used for pICH4661 and pICH4673 containing IRES-HPT fusions conferring resistance against hygromycin. In order to compare the efficiency of translational versus transcriptional vectors, the NPTII gene under control of NOS promoter was also incorporated into pICH3853 and pICH4021. The T-DNA of pICH3853 and pICH4021 were introduced in *Arabidopsis thaliana* (Col-0) plants as descried by Bent et al., (1994, *Science*, 285, 1856-1860). Seeds were harvested three weeks after vacuum-infiltration and divided in two equal groups. One group was sterilised and screened for transformants on GM+1% glucose medium (Valvekens et al., 1988, *Proc. Natl. Acad. Sci. USA*, 85, 5536-5540.) containing 50 mg L$^{-1}$ kanamycin. The other group was germinated in soil and sprayed several times by phosphinothricin solution (50 µg/ml). The number of transformants from each screening experiment was counted. The ratio of the number of transformants obtained with translational vectors to that obtained with transcriptional vectors (ppt$^R$:Km$^R$) was roughly in the range of 1:10-1:25 depending on the construct used.

All constructs described here were also used for *Nicotiana tabaccum Agrobacterium*-mediated leaf disc (Horsh et al., 1985, *Science*, 227, 1229-1231) and *Brassica napus* (cv. Westar) hypocotyl (Radke et al., 1988, *Theor. Appl. Genet.*, 75, 685-694) transformations. Despite a 10-20 fold difference in genome size of Arabidopsis compared to *Brassica napus* and tobacco, respectively, the frequency of transformants of *Brassica* and tobacco obtained with translational vectors, was comparable to that of *Arabidopsis* (10-15 times lower compared to transcriptional vectors).

Example 10

Production of Pharmaceuticals in Plants

The aim of this example is to demonstrate the possibility of producing pharmaceutical proteins in plants using a translational vector as an expression cassette.

Recloning of *Arabidopsis* ubiquitin11 (Gene Bank L05362)-human proinsulin (Gene Bank NM000207) and tobacco calreticulin signal peptide (Borisjuk et al., 1999, *Nat Biotechnol.*, 17, 466-469)-ubiquitin11-human proinsulin translational fusions as NcoI-BamHI fragments into NcoI-BamHI site of pCBV based binary vector pICH5410 (see FIG. 12), producing the constructs pICH5410-UPI and pICH5410-CUPI, respectively (FIG. 10).

Transformation of *Pennisetum glaucum*

Immature seeds of *Pennisetum glaucum* lines PEN3, PEN5, HGM100 (10-15 days post anthesis) were surface-sterilized by immersing into 70% ethanol for 5 min, followed by incubation in 1% sodium hypochlorite solution with shaking at 125 rpm for 20 min and finally by 3 washes in sterile distilled water. Immature embryos (1.0 mm in length, transparent) were isolated aseptically and were placed, with a scutellum side up, on a solid MS (Murashige and Skoog 1962) medium with 2 mg/l 2,4-D (MS2). The compact nodular calli were selected using a stereomicroscope and subcultured every month onto fresh MS2. The cultures were kept in dark at 25° C.

Plasmid preparation and microprojectile bombardment were performed as described in EXAMPLE, 3

Seven days after bombardment, the treated calli were transferred to the MS selection medium with 2 mg/l 2,4-D and 150 mg/l Hygromycin B and cultured in the dark. Two to four months later, growing callus tissues were subcultured to the MS regeneration medium supplemented with 5 mg/l zeatin, 1 mg/l kinetin, 0.1 mg/l 2,4-D and 100 mg/l Hygromycin B. Regenerating plantlets were transferred to jars with the half-strength hormone-free MS medium with 50 mg/l Hygromycin B. The fully developed plantlets were acclimated for 5-7 days in a liquid medium containing the four-fold diluted MS salts. Plants with strong roots were transplanted into soil and grown under greenhouse conditions to maturity.

In order to test the presence of proinsulin in transgenic plants, the total soluble protein was extracted from the homogenised leaf tissue, separated by SDS/PAGE and proteins were transferred to a nitrocellulose membrane in a Bio- Rad Trans-Blot cell (Tzen et al., 1990, *Plant Physiol.*, 94, 1282-1289). Immunoblot analysis was performed with monoclonal antibodies against proinsulin.

Appendix

Seed Sterilization

Soak the seeds in 1% PPM solution for at least 2 hours (overnight is preferable). Wash the seeds in 70% EtOH for 1 minute than sterilize in 10% chlorine solution with 0.01% SDS or Tween 20) in 250 ml flask placed on the rotary shaker. Wash the seeds in 0.5 L of sterile water.

| TVL | Enzyme solution |
|---|---|
| 0.3 M sorbitol | 1% cellulase R10 |
| 0.05 M CaCl$_2$ × 2H$_2$O | 0.2% macerase R10 |
| pH 5.6-5.8 | 0.1% dricelase |
| | dissolved in 8 pM macrosalt with 0.5 M |
| | pH 5.6-5.8 |

| W5 | PEG solution |
|---|---|
| 18.4 g/L CaCl$_2$ × 2H$_2$O | 40% (w/v) of PEG-2000 in H$_2$O |
| 9.0 g/L NaCl | |
| 1.0 g/L glucose | |
| 0.8 g/L KCl | |
| pH 5.6-5.8 | |

| CIM | | MIM | |
|---|---|---|---|
| Macro MS | | Macro MS | |
| Micro MS | | Micro MS | |
| Vitamin B5 | | Vitamin B5 | |
| MES | 500 mg/L | MES | 500 mg/L |
| PVP | 500 mg/L | PVP | 500 mg/L |
| Sucrose | 30 g/L | Sucrose | 30 g/L |
| 2,4-D | 5 mg/L | ABA | 1 mg/L |
| Kin | 0.25 mg/L | BA | 0.5 mg/L |
| Gelrite | 3 g/L | IAA | 0.1 mg/L |
| pH | 5.6-5.8 | Gelrite | 3 g/L |
| | | pH | 5.6-5.8 |

| Greening Medium (GM) | | High Auxine Medium (HAM) | |
|---|---|---|---|
| Macro MS | | Macro MS | |
| Micro MS | | Micro MS | |
| Vit B5 | | Vit B5 | |
| MES | 500 mg/L | MES | 500 mg/L |
| PVP | 500 mg/L | PVP | 500 mg/L |
| Sucrose | 30 g/L | Sucrose | 30 g/L |
| BA | 2 mg/L | NAA | 5 mg/L |
| Kin | 0.5 mg/L | Kin | 0.25 mg/L |
| NAA | 0.1 mg/L | BA | 0.25 mg/L |
| pH | 5.6-5.8 | pH | 5.6-5.8 |

| Regeneration Medium | |
|---|---|
| Macro MS | |
| Micro MS | |
| Vit B5 | |
| MES | 500 mg/L |
| PVP | 500 mg/L |
| Sucrose | 30 g/L |
| ABA | 1 mg/L |
| BA | 0.5 mg/L |
| IAA | 0.1 mg/L |
| pH | 5.6-5.8 |

Hormone solutions were filter sterilized and added to autoclaved media.

The invention claimed is:

1. A process for producing transgenic plant comprising and expressing a transgenic coding sequence of interest under transcriptional control of an endogenous plant nuclear promoter, comprising (a) introducing into the nuclear genome of a plant cell a vector comprising a nucleotide sequence that encodes a nucleic acid sequence that binds a plant cytoplasmic ribosome, said vector further comprising a translational stop signal upstream of said nucleic acid sequence, wherein said nucleic acid sequence that binds a plant cytoplasmic ribosome is a plant viral internal ribosome entry site (IRES) of a crucifer-infecting tobamovirus, said vector further comprising a transgenic coding sequence of interest downstream of said nucleotide sequence, wherein the transgenic coding sequence of interest is not operationally linked to a promoter in the vector and is transcribed by the endogenous plant promoter and translated by the IRES of the vector; and (b) selecting a plant expressing said transgenic coding sequence of interest.

2. The process according to claim 1, wherein said vector additionally comprises one or more cistrons downstream of said transgenic coding sequence, whereby said one or more cistrons are operably joined to nucleic acid sequences that bind a plant cytoplasmic ribosome or are under control of one or more promoters.

* * * * *

UNITED STATES PATENT AND TRADEMARK OFFICE
CERTIFICATE OF CORRECTION

PATENT NO. : 7,652,194 B2  
APPLICATION NO. : 10/416931  
DATED : January 26, 2010  
INVENTOR(S) : Gleba et al.

It is certified that error appears in the above-identified patent and that said Letters Patent is hereby corrected as shown below:

On Title Page:

Item 57, Abstract, Line 6: Please delete "preferably".

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,652,194 B2  Page 1 of 1
APPLICATION NO. : 10/416931
DATED : January 26, 2010
INVENTOR(S) : Gleba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 525 days.

Signed and Sealed this

Twenty-third Day of November, 2010

David J. Kappos
*Director of the United States Patent and Trademark Office*